(12) United States Patent
Kitchel

(10) Patent No.: US 9,778,053 B2
(45) Date of Patent: *Oct. 3, 2017

(54) GENERATING USER PREFERENCE ACTIVITY MAPS

(71) Applicant: Strava, Inc., San Francisco, CA (US)

(72) Inventor: Davis Kitchel, Norwich, VT (US)

(73) Assignee: Strava, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/045,067

(22) Filed: Feb. 16, 2016

(65) Prior Publication Data

US 2016/0161273 A1 Jun. 9, 2016

Related U.S. Application Data

(63) Continuation of application No. 14/564,863, filed on Dec. 9, 2014, now Pat. No. 9,297,651.

(60) Provisional application No. 61/914,859, filed on Dec. 11, 2013.

(51) Int. Cl.

| G01C 21/00 | (2006.01) |
|---|---|
| H04W 4/02 | (2009.01) |
| G01C 21/34 | (2006.01) |
| G01C 5/06 | (2006.01) |
| G01C 21/36 | (2006.01) |
| G01S 19/13 | (2010.01) |

(52) U.S. Cl.
CPC ........... *G01C 21/3461* (2013.01); *G01C 5/06* (2013.01); *G01C 21/34* (2013.01); *G01C 21/3484* (2013.01); *G01C 21/3667* (2013.01); *G01S 19/13* (2013.01); *H04W 4/028* (2013.01)

(58) Field of Classification Search
CPC   G01C 21/3461; G01C 21/3667; G01C 21/34; G01C 21/3484; G01C 5/06; G01S 19/13; H04W 4/028
See application file for complete search history.

(56) References Cited

U.S. PATENT DOCUMENTS

| 5,178,010 | A | 1/1993 | Holzel | |
|---|---|---|---|---|
| 7,454,002 | B1 | 11/2008 | Gardner et al. | |
| 7,610,151 | B2 * | 10/2009 | Letchner | G01C 21/3484 701/424 |
| 9,513,137 | B2 * | 12/2016 | Hisano | G06Q 30/0266 |
| 2012/0253488 | A1 | 10/2012 | Shaw | |
| 2013/0345978 | A1 * | 12/2013 | Lush | G01C 21/00 701/533 |
| 2014/0288680 | A1 * | 9/2014 | Hoffman | G06K 9/00342 700/91 |

* cited by examiner

*Primary Examiner* — Michael J Zanelli
(74) *Attorney, Agent, or Firm* — Van Pelt, Yi & James LLP

(57) ABSTRACT

Generating user preference activity maps is disclosed, including: collecting a plurality of user activities recorded by a plurality of GPS recording devices; and aggregating the plurality of user activities to a base map to generate a user preference map.

30 Claims, 18 Drawing Sheets

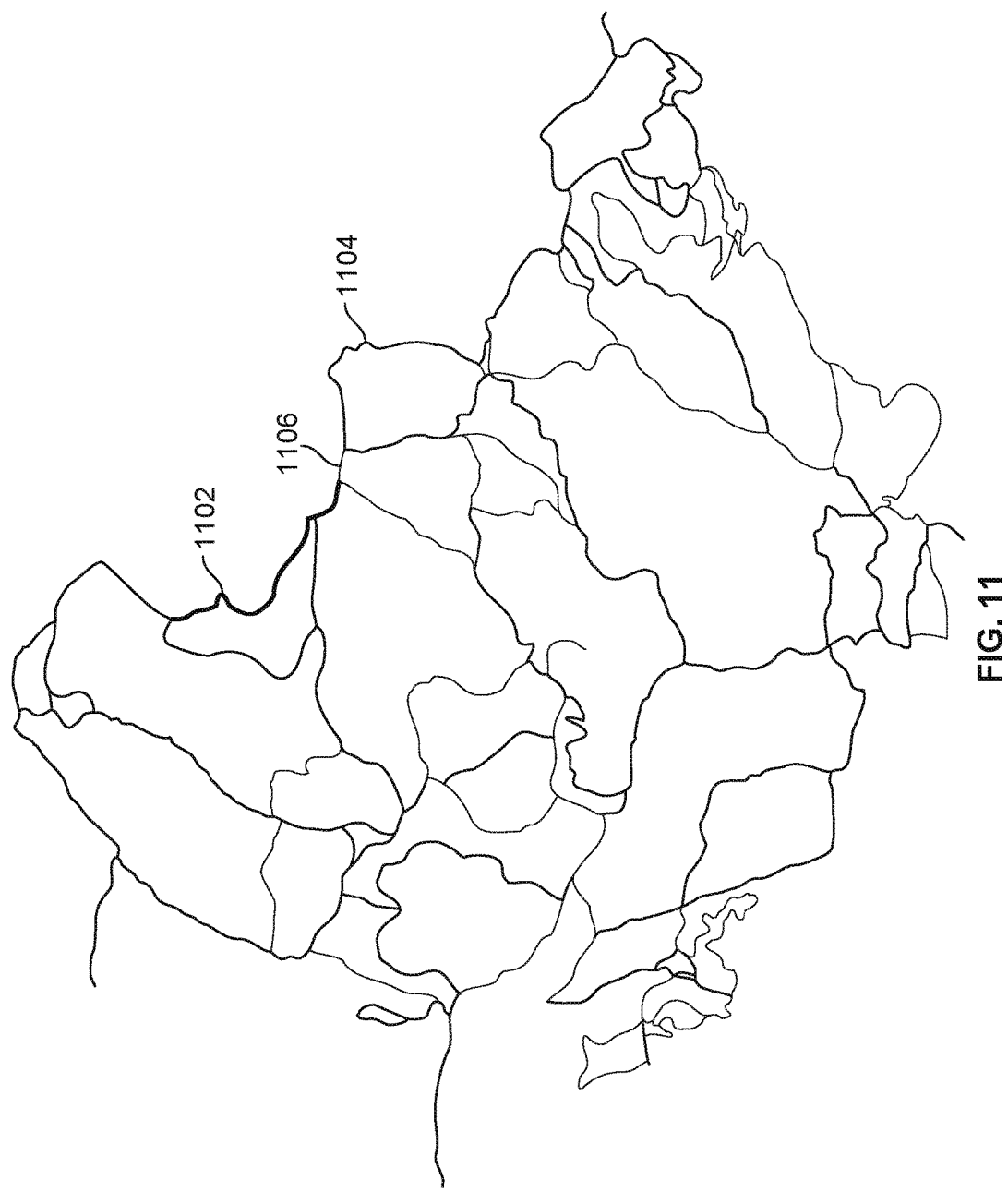

GENERATING USER PREFERENCE ACTIVITY MAPS

CROSS REFERENCE TO OTHER APPLICATIONS

This application is a continuation of co-pending U.S. patent application Ser. No. 14/564,863, entitled GENERATING USER PREFERENCE ACTIVITY MAPS filed Dec. 9, 2014 which is incorporated herein by reference for all purposes, which claims priority to U.S. Provisional Patent Application No. 61/914,859 entitled GENERATING ATHLETIC ACTIVITY HEAT MAPS filed Dec. 11, 2013 which is incorporated herein by reference for all purposes.

BACKGROUND OF THE INVENTION

Typical mapping technology uses functional classification to classify a road into the class or group of roads to which the road belongs. Examples of such functional classes include arterial, collector, and local. However, by using such mapping technology, conventional routing technology for athletes such as cyclists and runners is not usually based on the actual behavior of athletes.

The actual behavior of athletes is also difficult to track. To track the behavior of cyclists, for example, governmental transportation departments commonly place sensors on select roads and/or deploy people to different areas to manually count the number of passerby cyclists. However, these techniques may be inefficient, laborious, and/or may not provide a broad sampling of the actual behavior of athletes.

Having accurate elevation profiles for a planned route can be essential for planning for an athletic activity. Sometimes a person may want a relatively flat route, and sometimes a person may want a hilly route. When planning for a hilly route, it is important to know the steepest grade that will be encountered. Examples of why knowing the steepest grade in a planned route is useful are that the knowledge enables cyclists to choose the proper bike gearing for the ride, and helps both runners and cyclists dose their efforts during the route. However, global elevation profiles on roads and trails with the necessary accuracy for cyclists and runners do not currently exist.

BRIEF DESCRIPTION OF THE DRAWINGS

Various embodiments of the invention are disclosed in the following detailed description and the accompanying drawings.

FIG. 11 is a diagram showing an example of a presentation of a user preference map in accordance with some embodiments.

DETAILED DESCRIPTION

Figure 1:
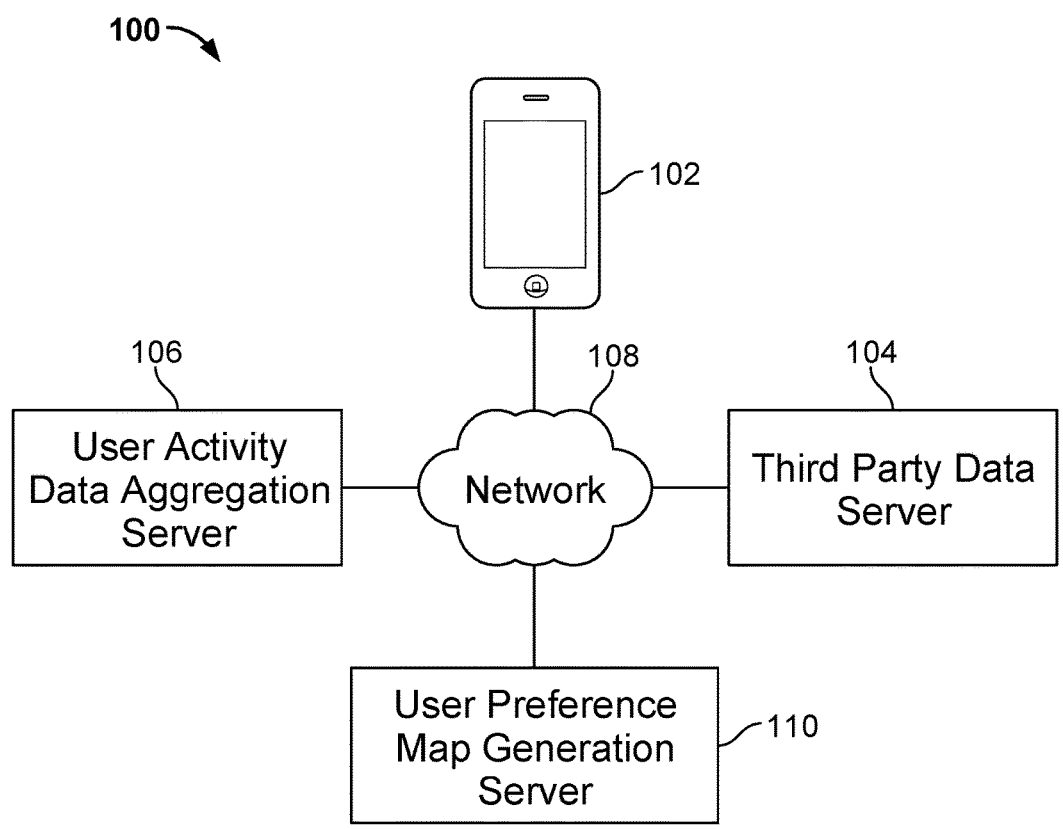
FIG. 1 is a diagram showing a system for generating a user preference map in accordance with some embodiments.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Embodiments of generating a user preference map are described herein. User activities collected by geographical positioning satellite (GPS) recording devices are collected. For example, each user activity comprises a set of GPS data (e.g., a series of GPS coordinates) along which the activity occurred, a corresponding set of time information (e.g., a timestamp corresponding to each GPS coordinate), and, optionally, other data associated with the user activity. The collected user activities are analyzed and aggregated with respect to each of at least a subset of edges in an obtained base map to generate a user preference map. For example, the base map may comprise a set of geographic information system (GIS) data that can be obtained from a third party source. The base map includes a number of edges, each of which represents a path, road, or trail. In various embodiments, a user input first endpoint (e.g., a start point/location) and a user input second endpoint (e.g., an end point/location) are received and one or more suggested routes from the user input first endpoint to the user input second endpoint are determined using the user preference map. In some embodiments, in addition to a first endpoint and a second endpoint, one or more user input route preferences are also received. Examples of route preferences include a desired route length, a desired surface type, a desired elevation type, a desired popularity, a desired power usage, and/or whether the route should be scenic. In some embodiments, one or more suggested routes can then be determined based on the user input first endpoint, the user input second endpoint, and the user input one or more route preferences. In some embodiments, the suggested routes may be visually displayed on a map at a user interface.

Embodiments of generating a set of elevation data associated with an edge are described herein. Collected user activities that match an edge (e.g., in a base map) are determined. At least one of such matching user activities that includes elevation/barometric data is selected. The selected matching user activity associated with the recorded barometric data is used with looked up elevation data (e.g., elevation data looked up from a third party source such as the United States Geological Survey (USGS)) to determine a set of elevation data for the edge. In some embodiments, the elevation data determined for the edge is also stored in the user preference map with the other user activity data aggregated for that edge.

A generated user preference map may have several applications. In a first example, the user preference map can be used by a smart route planner to generate a suggested route, which adds the aggregated edge popularity in a dynamic cost structure which may also include elevation gain preferences and other preference inputs. In a second example, the user preference map can be used by a product for the purpose of analyzing and displaying recorded alternative transportation corridors in metro areas. This type of product may facilitate the identification and improvement of cycling corridors by local departments of transportation (DOTs) and or engineering firms specializing in such analysis and infrastructure analysis and recommendation, for instance. In a third example, the user preference map can be used by products that leverage the aggregated elevation data, including accurate road grade information, to determine fuel savings on routes. In a fourth example, the user preference map can be used by mobile dynamic routing for athletes in real-time, during user activities.

FIG. 1 is a diagram showing a system for generating a user preference map in accordance with some embodiments. In the example, system 100 includes device 102, user activity data aggregation server 106, network 108, third party data server 104, and user preference map generation server 110. Network 108 may include high-speed data networks and/or telecommunication networks.

Device 102 is a device that can record GPS data and/or other data associated with an athlete user activity. Device 102 can also be a device to which GPS data and/or other data associated with a physical activity can be uploaded or transferred. Examples of device 102 include, but are not limited to: a GPS device (e.g., Garmin Forerunner® and Edge® devices, including Garmin Forerunner® 110, 205, 301, 305, 310XT, 405, 405CX, and Garmin Edge® 305, 605, 705, 500, 800, 810, and 1000), a mobile phone, such as a smart phone (e.g., an Android®-based device or Apple iPhone® device) including a GPS recording application (e.g., MotionX®, Endomondo®, Strava®, and RunKeeper®), a computer, a tablet device, and/or other general purpose computing devices and/or specialized computing devices, which typically include a general processor, a memory or other storage component(s), a network or input/output (I/O) capability, and possibly integrated GPS functionality or support or an interface for a GPS device or GPS functionality.

In various embodiments, device 102 (or an application thereof) is configured to record GPS data and auxiliary data associated with a user activity during the activity. For example, auxiliary data associated with a user activity may include physiological, environmental, and/or performance data. In some embodiments, device 102 is configured to receive recorded GPS data and auxiliary data associated with a user activity subsequent to the completion of the activity (e.g., such information is uploaded to device 102).

In some embodiments, a "user activity" refers to a completed athletic performance. Examples of a user activity include cycling, running, and skiing. In some embodiments, GPS data includes a series of consecutive and discrete GPS data points (e.g., latitude and longitude coordinates sometimes referred to as "Lat-Lng Data") with a timestamp for each point. In some embodiments, auxiliary data includes, but is not limited to, barometric data (e.g., elevation data), heart rate, power/watts (e.g., energy expended), time, speed (e.g., average and/or maximum speed per segment and/or route, in which average speed, for example, can be derived from time and GPS information), and/or cadence. Auxiliary data can be recorded at various granularities. For example, auxiliary data can correspond to each GPS data point, the entire activity (e.g., the auxiliary data includes averages of the metrics), and/or portions of the activity. As an example, one can use device 102 on a bike ride. At the end of the bike ride, the user can review his performance with the recorded GPS data (e.g., through a user interface of device 102) to observe the geographical track that he traversed, how much energy he expended along the ride, how fast he finished it in, average speed, elevation-based metrics, and/or other metrics. In some embodiments, device 102 is configured to store the recorded GPS data and the auxiliary data and/or send the recorded data associated with a user activity to user activity data aggregation server 106. In some embodiments, device 102 is configured to send the recorded data associated with a user activity to user activity data aggregation server 106 during the user activity (e.g., in real-time) and/or after the user activity has been completed. In some embodiments, device 102 is configured to present an interactive user interface. The user interface may display GPS data and receive selections (e.g., made by a user) with respect to the displays. In some embodiments, device 102 sends the selections that it receives to user preference map generation server 110.

In some embodiments, a user interface may be presented at device 102. In some embodiments, the user interface may be presented by user preference map generation server 110 or by another component that is not shown in the example of FIG. 1. In some embodiments, the user interface is configured to receive user inputs such as a first endpoint and second endpoint associated with a desired route and/or one or more route preferences associated with the desired route. In some embodiments, the user interface is configured to receive user inputs such as a time interval. The user inputs received at device 102 are configured to be sent to user preference map generation server 110.

User activity data aggregation server 106 is configured to aggregate recorded user activity data from devices such as device 102. In some embodiments, the recorded user activity data received at user activity data aggregation server 106 is received during the user activities (e.g., in real-time) and/or subsequent to the completion of the user activities. User activity data aggregation server 106 is configured to store information associated with each user activity. For example, information associated with each user activity includes an identifier associated with the athlete that performed the activity, the activity type associated with the activity, the date and/or period of time during which the activity took place, the device type that was used to record the activity data, and the equipment used by the athlete during the activity. In some embodiments, the information associated with each user activity may include attributes associated with the user activity that were input by a user and/or attributes associated with the user activity that were inferred from the recorded data. In some embodiments, the information associated with each activity is stored by user activity data aggregation server 106 in an activity table that comprises a SQL-based data table. User activity data aggregation server 106 is configured to store the set of GPS data (e.g., a set of GPS/Lat-Lng data points) and a corresponding auxiliary data (e.g., barometric/elevation data, timestamps, watts, heart rates, power, etc.) associated with (e.g., recorded GPS data point along) each user activity. In some embodiments, the set of GPS data and a corresponding set of auxiliary data associated with each user activity are stored by user activity data aggregation server 106 in a virtual hard drive (e.g., Amazon Simple Storage Service) associated with dynamically expanding storage availability. User activity data aggregation server 106 is configured to process the data received for each user activity and perform spatial indexing for each user activity based on the set of GPS data associated with the user activity. In some embodiments, in performing spatial indexing, the information from the activity table and the GPS and corresponding auxiliary data from the virtual hard drive are put together and recorded for each recorded GPS data point and put into a PostGIS database or other spatially enabled and indexed data structure. User activity data aggregation server 106 is configured to send the aggregated user activity data to user preference map generation server 110.

User preference map generation server 110 is configured to receive the aggregated user activity data from user activity data aggregation server 106. User preference map generation server 110 is configured to obtain a base map from a third party data server such as third party data server 104. For example, the base map may comprise a set of GIS data that describes roads and paths with edges. For example, the base map may comprise a set of GIS data from Topologically Integrated Geographic Encoding and Referencing (TIGER) or Open Street Map. As will be described in detail below, to generate a user preference map, user preference map generation server 110 is configured to data mine at least a subset of user activity data associated with each region of the base map. User preference map generation server 110 is configured to determine a set of user activities that match each of at least a subset of edges in the region and store the metadata (e.g., user activity information, GPS data, and auxiliary data) associated with those matching user activities with the edge in a user preference map. In some embodiments, the user preference map comprises the obtained base map stored with the metadata associated with user activities that match each edge of the base map.

In various embodiments, user preference map generation server 110 is configured to determine for each of at least a subset of edges of the base map, a set of elevation data. Determining a set of elevation data for an edge includes selecting a user activity that matches the edge and that is associated with recorded elevation/barometric data. The barometric data recorded with the selected user activity is presumed to be associated with relative accuracy. Determining a set of elevation data for an edge also includes querying for elevation data associated with the edge from a third party data server such as third party data server 104. For example, a third party service that provides elevation data is the USGS. The queried or otherwise looked up elevation data associated with the edge is presumed to be associated with absolute accuracy. As will be described in detail below, the set of elevation data for an edge is determined based at least in part on the barometric data associated with the selected matching user activity and the looked up elevation data associated with the edge. In some embodiments, the set of elevation data determined for an edge is stored with the metadata associated with user activities that match that edge in the user preference map.

User preference map generation server 110 is configured to receive user inputs from a device such as device 102. In some embodiments, the received user inputs are associated with route preferences. In some embodiments, the received user inputs are associated with a specified time interval. As will be described below, in some embodiments, in response to the user inputs from device 102 for route preferences, user preference map generation server 110 is configured to present on a presented map visual representations of one or more suggested routes that match the user inputs from a generated user preference map. As will be described below, in some embodiments, in response to the user inputs from device 102 associated with a time interval, user preference map generation server 110 is configured to present on a presented map visual representations of user activities that match the received time interval from a generated user preference map. In some embodiments, user preference map generation server 110 is able to support presentation of a map at the user interface by including logic configured to interact with the Application Programming Interface (API) of a map software/application (e.g., Google® Maps, MapQuest®, Bing® maps, and/or another mapping application/service).

Figure 2:
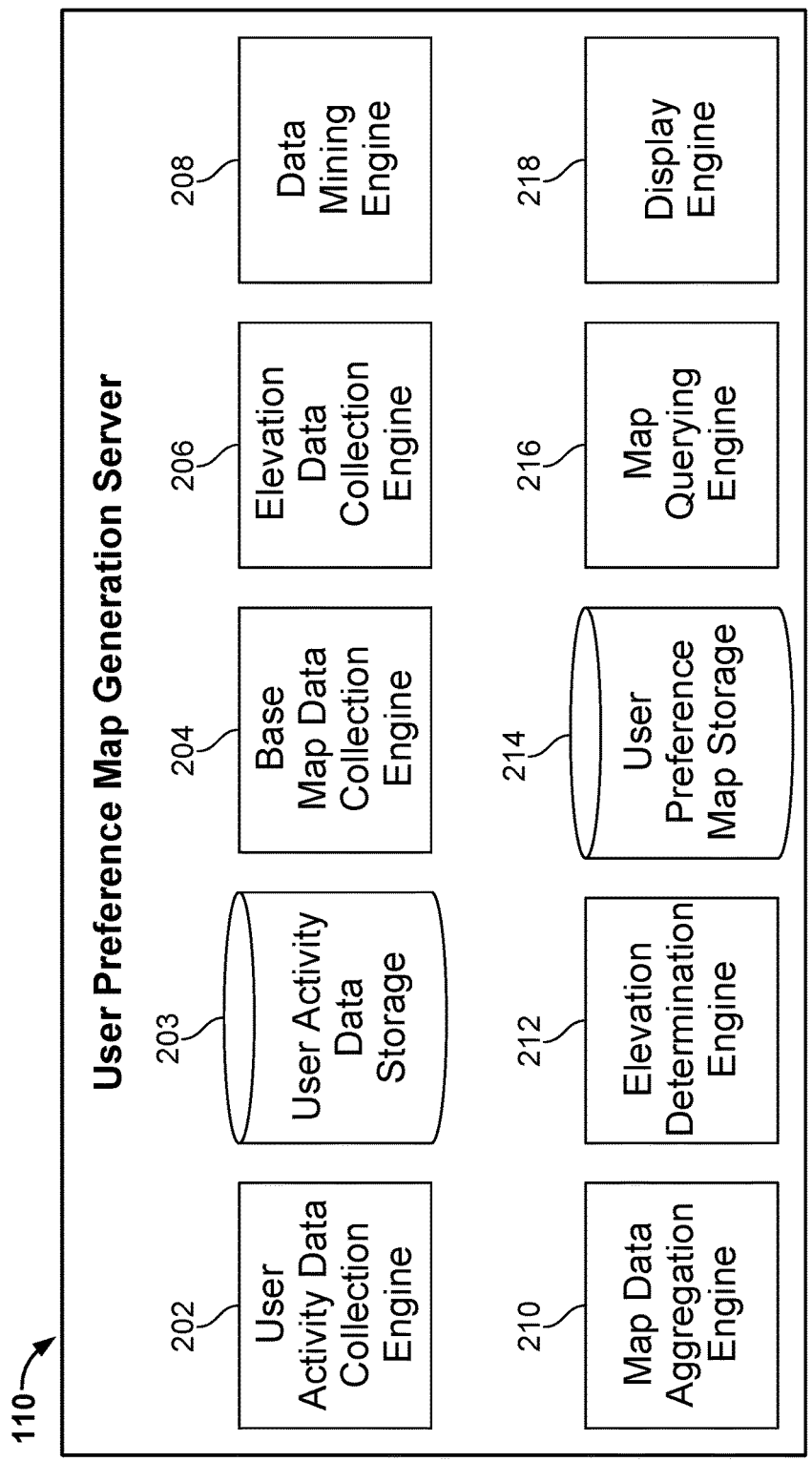
FIG. 2 is a diagram showing an example of a user preference map generation server in accordance with some embodiments.

FIG. 2 is a diagram showing an example of a user preference map generation server in accordance with some embodiments. In some embodiments, user preference map generation server 110 of system 100 of FIG. 1 can be implemented with the example of FIG. 2. In the example of FIG. 2, the user preference map generation server includes user activity data collection engine 202, user activity data storage 203, base map data collection engine 204, elevation data collection engine 206, data mining engine 208, map data aggregation engine 210, elevation determination engine 212, user preference map storage 214, map querying engine 216, and display engine 218. Each of user activity data collection engine 202, base map data collection engine 204, elevation data collection engine 206, data mining engine 208, map data aggregation engine 210, elevation determination engine 212, map querying engine 216, and display engine 218 can be implemented, for example, as distinct or integrated software components, which can include module(s), package(s), and/or other sub-components to provide an executable computer program that can perform these described functions when executed on a processor, and can be implemented using a programming language such as Java, Python, Objective C, and/or other programming languages. An example hardware computing environment to execute the engines of FIG. 2 includes a cloud computing service, such as Amazon's Web Services.

User activity data collection engine 202 is configured to collect user activity data recorded by GPS-enabled devices. Each set of activity data includes for example, one of the following: a set of GPS data, auxiliary data corresponding to the GPS data, and user activity information. In some embodiments, user activity data collection engine 202 is configured to receive real-time user activity data as the user activities are still ongoing. In some embodiments, user activity data collection engine 202 is configured to receive data associated with completed user activities. The collected user activity data may be associated with one or more types of activities (e.g., cycling, running, swimming, etc.). In some embodiments, the collected user activity data is stored at user activity data storage 203.

Base map data collection engine 204 is configured to obtain a base map by querying a third party source. For example, the base map may comprise a set of GIS data from TIGER or Open Street Map, for example. For example, a base map may include streets, highways, boundaries for census, postal, political areas, rivers, lakes, parks, landmarks, place names, and U.S. geological survey (USGS) raster maps. The base map includes a number of edges, each of which represents a path, road, or trail.

Elevation data collection engine 206 is configured to look up elevation data corresponding to each of at least a subset of edges in the base map obtained by base map data collection engine 204. For example, the elevation data may be obtained by querying a USGS server.

Data mining engine 208 is configured to mine the user activity data aggregated by user activity data collection engine 202 and/or stored at user activity data storage 203. In some embodiments, data mining engine 208 is configured to mine an amount of user activities associated with the same type of activity (e.g., cycling or running) associated with each region of the base map obtained by base map data collection engine 204. In some embodiments, the amount of user activities to mine can be determined based on a preset rule.

Map data aggregation engine 210 is configured to aggregate the user activities mined by data mining engine 208 with matching edges of the base map obtained by base map data collection engine 204. In some embodiments, map data aggregation engine 210 is configured to determine which mined user activities match each of at least a subset of edges in the base map. A user activity is determined to match an edge if it meets a set of edge matching criteria. In various embodiments, the metadata (e.g., the GPS data, the corresponding auxiliary data, the user activity information) associated with the set of user activities that have been determined to match an edge is stored with the edge in a user preference map. Map data aggregation engine 210 is configured to store the user preference map at user preference map storage 214. In some embodiments, a user preference map is determined for each activity type.

Elevation determination engine 212 is configured to determine a set of elevation data associated with each of at least a subset of edges in the base map obtained by base map data collection engine 204. In various embodiments, elevation determination engine 212 is configured to select one user activity that was determined by map data aggregation engine 210 to match an edge and is also associated with recorded barometric data as a selected barometric data candidate user activity. In some embodiments, elevation determination engine 212 is configured to use elevation data obtained by elevation data collection engine 206 for the edge to adjust the recorded elevation corresponding to each GPS data point of the selected barometric data candidate user activity associated with the edge to obtain the set of elevation data for that edge. In some embodiments, elevation determination engine 212 is configured to store the set of elevation data determined for an edge with the other metadata stored with the edge at the corresponding user preference map stored at user preference map storage 214.

Map querying engine 216 is configured to receive user inputs associated with route preferences and/or time intervals associated with an activity type. In some embodiments, map querying engine 216 is configured to query the user preference map associated with the activity type stored at user preference map storage 214 based on the user inputs and use the queried user preference map to generate visual representations on a map associated with data that matches the user inputs. For example, the user inputs may describe a desired route from a first endpoint to a second endpoint and/or route preferences for cycling (e.g., a popular five mile ride with low elevation) and the generated visual presentations could present one or more suggested routes on a map that are about five miles in length, traverse paths with a low elevation, and are in the top 10% of more frequently traversed paths. For example, the user inputs may include a time interval of March 2014 and the activity type of running and the generated visual presentations could present the degree to which each path on a map was traversed by runners during the period of March 2014. In various embodiments, map querying engine 216 is configured to compare the user inputs to metadata stored for each of at least a subset of edges in the user preference map to determine one or more routes, each comprising one or more edges, which match the user inputs. In some embodiments, map querying engine 216 is configured to receive user inputs from a user while the user is currently performing a user activity. Map querying engine 216 is configured to send the presentation data generated in response to user inputs to display engine 218. Display engine 218 is configured to present the presentation data at a user interface.

Figure 3:
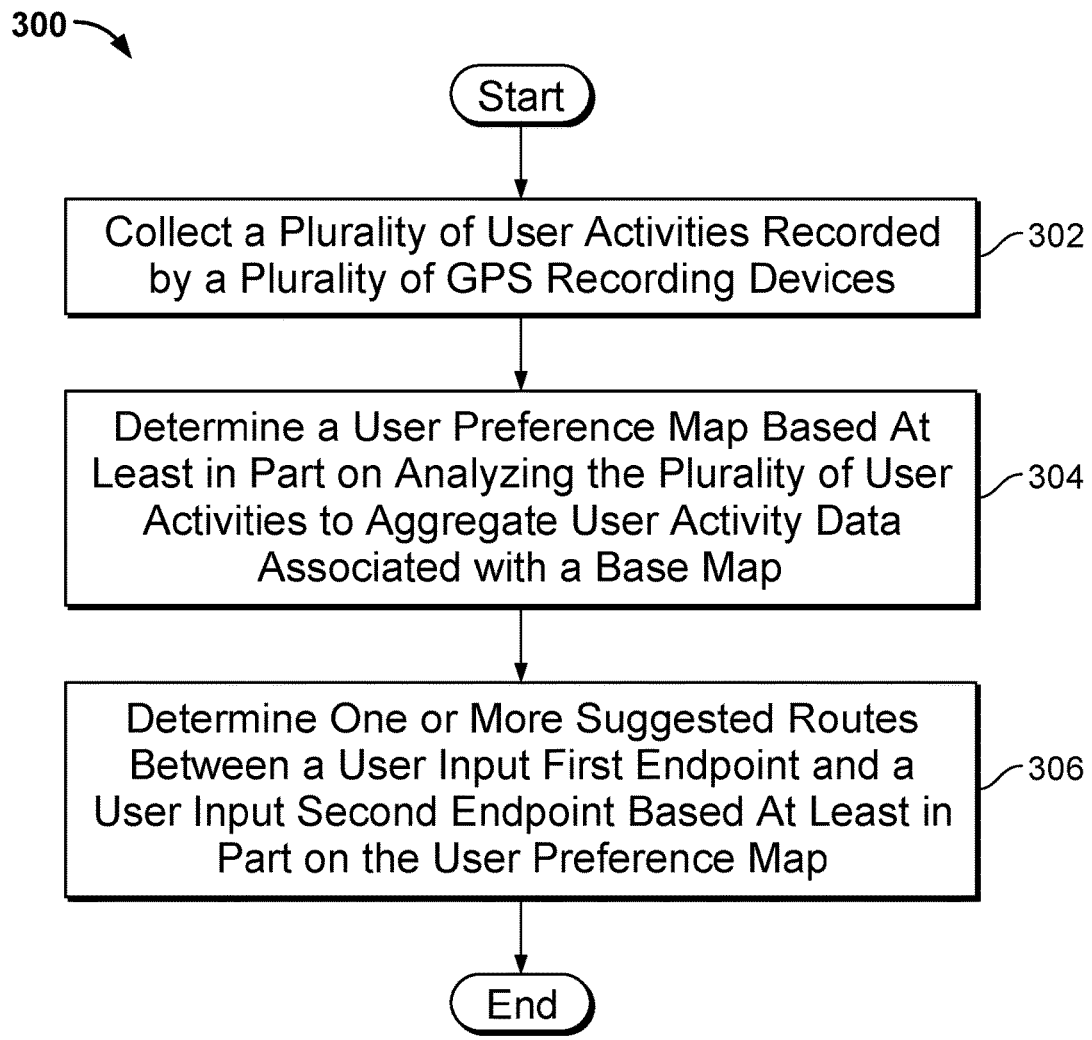
FIG. 3 is a flow diagram showing a process for using a user preference map in accordance with some embodiments.

FIG. 3 is a flow diagram showing a process for using a user preference map in accordance with some embodiments. In some embodiments, process 300 is implemented at system 100 of FIG. 1.

At 302, a plurality of user activities recorded by a plurality of GPS recording devices is collected. In various embodiments, each user activity is recorded with at least a set of GPS data (e.g., GPS data points) and a set of corresponding auxiliary data (e.g., barometric data, heart rate, power/watts, time, speed, and/or cadence corresponding to each GPS data point). For example, data associated with a user activity is recorded using a GPS-enabled device while the user is performing the user activity. In various embodiments, each user activity is also recorded with user activity information such as, for example, an identifier associated with the athlete that performed the activity, the activity type associated with the activity, the date and/or period of time during which the activity took place, the device type that was used to record the activity data, and the equipment used by the athlete during the activity.

At 304, a user preference map is determined based at least in part on analyzing the plurality of user activities to aggregate user activity data associated with a base map. In various embodiments, a base map comprises a set of GIS data. For example, the base map is obtained from a third party source. In various embodiments, the base map includes various edges, each of which represents a path, road, or trail. In various embodiments, the portion of the collected user activities that match each edge of the base map is determined and metadata associated with the user activities that match each edge is stored with that edge in a user preference map. For example, metadata stored with each edge in the user preference map may include the number of user activities that was determined to match the edge, the auxiliary data associated with each user activity that was determined to match the edge, and user activity information associated with each activity that was determined to match the edge.

In some embodiments, a user activity that was determined to match an edge is selected and used with looked up elevation data associated with an edge to determine a set of elevation data associated with the edge. The set of elevation data associated with the edge comprises, in various embodiments, an elevation profile of the edge. In some embodiments, the determined set of elevation data associated with the edge is also stored with that edge in the user preference map. In various embodiments, a user preference map is determined for each activity type.

At 306, one or more suggested routes are determined between a user input first endpoint and a user input second endpoint based at least in part on the user preference map. In various embodiments, user inputs include at least a first endpoint (e.g., a start point/location) and a second endpoint (e.g., an end point/location), and optionally, one or more route preferences (e.g., desired route length, desired route elevation, desired activity type, desired popularity level, and/or associated with desired time frame, etc.) associated with a desired route. The generated user preference map (e.g., associated with the desired activity type) is used to find one or more suggested routes that match the user inputs. The suggested routes may be displayed at a user interface for the user.

Figure 4:
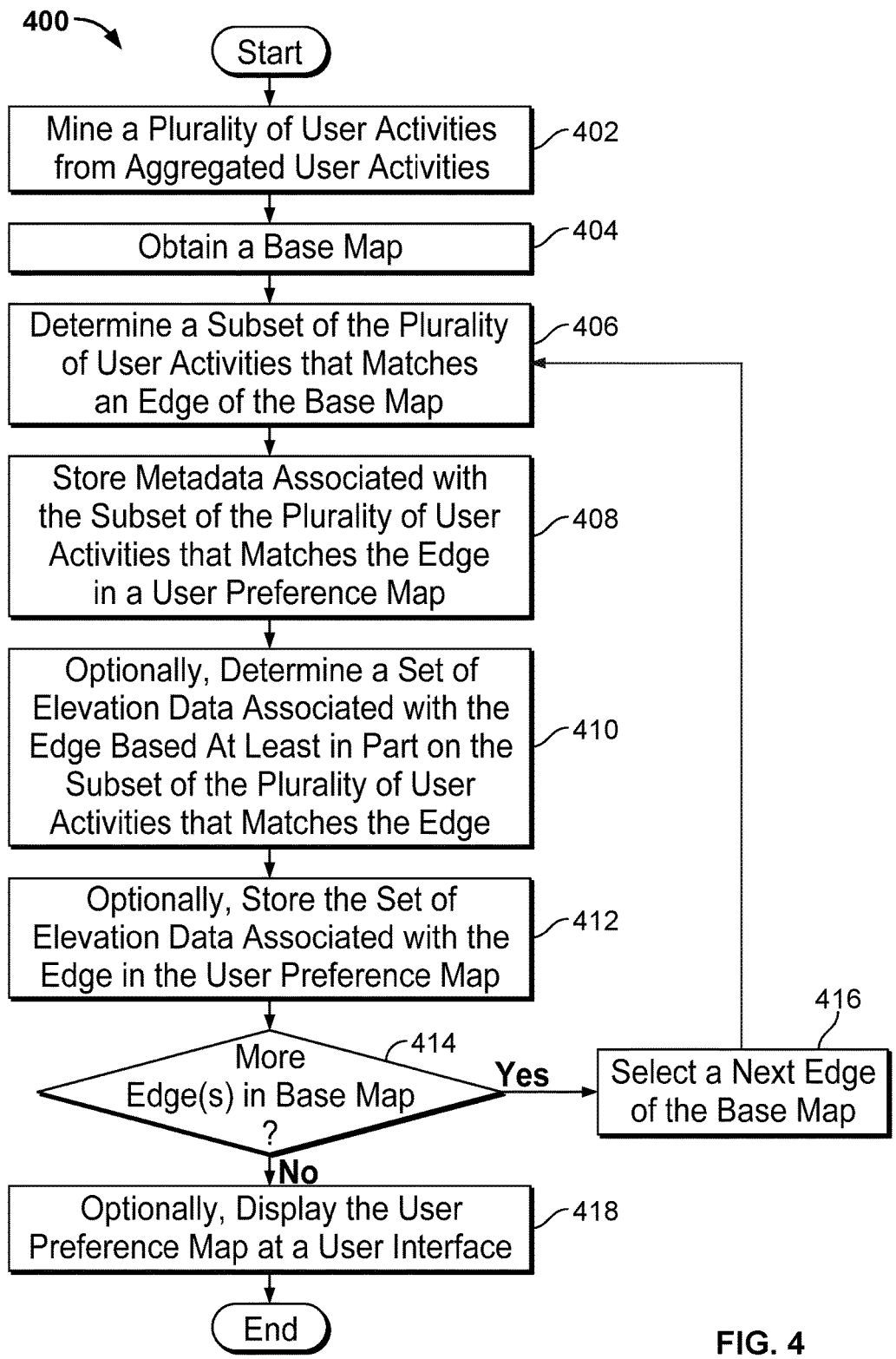
FIG. 4 is a flow diagram showing an example of a process for generating a user preference map in accordance with some embodiments.

FIG. 4 is a flow diagram showing an example of a process for generating a user preference map in accordance with some embodiments. In some embodiments, process 400 is implemented at system 100 of FIG. 1.

Process 400 describes an example process of data mining collected user activities and aggregating the collected user activities with edges of a base map to generate a user preference map. In various embodiments, a user preference map is associated with a particular activity type (e.g., cycling or running) and so the only activities associated with the same activity type are used to generate the user preference map associated with that activity type. For example, a separate user preference map may be generated for each of cycling activities and running activities.

At 402, a plurality of user activities is mined from aggregated user activities. User activities of the same activity type are mined. In some embodiments, while a large number of user activities (of the same activity type) may have been aggregated, data associated with only a subset of the aggregated user activities needs to be mined and used to generate the user preference map (associated with that activity type). This is because, in some instances, a sufficient enough sampling of the user activities can provide about the same level of user preference data as the entire body of user activities. In some embodiments, the amount of user activities to mine from a certain geographic region (e.g., polygons encompassing counties, metro areas, and trail networks are examples of regions) is determined based on a ratio of the number of user activities to a total length of edges in that region. Different ratios of a number of user activities to a total length of edges may be preset for each activity type. For example, one activity can be mined per each kilometer (km) of road in a region for cycling or one activity can be mined per each 100 meters of road in the region. For example, if there is a total of 1,000 km of road in a region, then 1,000 user activities that have occurred along any road in the region will be mined from the aggregated cycling activities. The mined user activities may be associated with one or more different users. The amount of mined user activity data is enough data to determine road and trail preferences. In some embodiments, all data is mined for a specific time period such as commute hours during weekdays to enable the user preference map to model cycling commute patterns for a specific metro area, for example.

In some embodiments, user activities are mined in an order associated with the type of GPS recording device that recorded the user activity data. Different device types may be associated with different levels of accuracy (e.g., associated with GPS data recording and/or auxiliary data recording) and so in some embodiments, a list of device types, in descending order of predicted accuracy, is used to perform data mining. In some embodiments, the accuracy of a device is determined based on a recorded granularity (e.g., more GPS data points recorded between shorter time intervals is indicative of better accuracy) and the relative spatial accuracy of the recorded GPS data points (e.g., better spatial accuracy of the recorded GPS data points is indicative of better overall accuracy). For example, assume that Garmin Edge 805 and 810 are the device types that are associated with the greatest predicted accuracies horizontally and vertically and so user uploaded activity data that was recorded by either the Garmin Edge 805 or 810 GPS-enabled devices is mined first. Then, if the desired amount of user activity data has not yet been mined, additional user activity data may be mined from the user uploaded activity data associated with the device type that is predicted to be the second most accurate on the list of device types, and so forth. In some embodiments, user uploaded activity data that was recorded by mobile devices may be mined last because of the mobile device's predicted lower accuracy and (often) lack of recorded barometric elevation data.

In some embodiments, data associated with all aggregated user activities (of the same activity type) associated with a preset window of time (e.g., the past year) are mined, regardless of the GPS recording device that was used to record the user activity data, and used to generate the user preference map.

In some embodiments, the data mined from user uploaded activity data may include one or more of the following example attributes:

activity_id: activity:
The "activity_id: activity" attribute enables counting of distinct activities.

athlete_id: activity:
The "athlete_id: activity" attribute enables counting of distinct athletes.

activity_type:
The "activity_type" attribute indicates whether the user activity comprises a run or ride, for example.

device_type:
The "device_type" attribute identifies the device used to record the GPS data points associated with the user activity.

start_date:
The "start_date" attribute indicates the date of the user activity and not the date of the upload of the activity data.

time:
The "time" attribute indicates the number of seconds into the activity at which each GPS data point was recorded.

start_end_times:
The "start_end_times" attribute indicates the start time and the end time during which the user activity took place/was recorded.

altitude:
The "altitude" attribute indicates the recorded elevation for each GPS data point associated with the user activity. GPS-enabled recording devices that have barometric altimeters may record altitude data for each GPS data point associated with the user activity.

heart_rate:
The "heart_rate" attribute indicates the recorded heart rate (when present) of the user at each GPS data point that was recorded.

watts:
The "watts" attribute indicates the number of watts (when present) of the user at each GPS data point that was recorded.

bearing:
The "bearing" attribute indicates the direction of travel from the last recorded GPS data point of the activity to the current GPS data point. In some embodiments, the bearing corresponding to each GPS data point is calculated during the data mining process (rather than recorded during the user activity). The bearing data may be used to further distill ground truth by finding gravitational centers of points that are all going in the same basic direction. This turns tight hairpins, which can be a blur of points, into a perfect representation of the real hairpin. In some embodiments, bearing may be calculated to the whole ground truth layer, or in strategic locations to clearly identify road and trail corridors where the ground truth layer has a large collection of points making it difficult in some cases.

geometry:
The "geometry" attribute indicates the location of the GPS data point spatially indexed for fast searching.

At 404, a base map is obtained. The base map comprises a set of GIS data. In various embodiments, the set of GIS data may be in any format. In various embodiments, the set of GIS data is obtained from a third party source.

Figure 7:
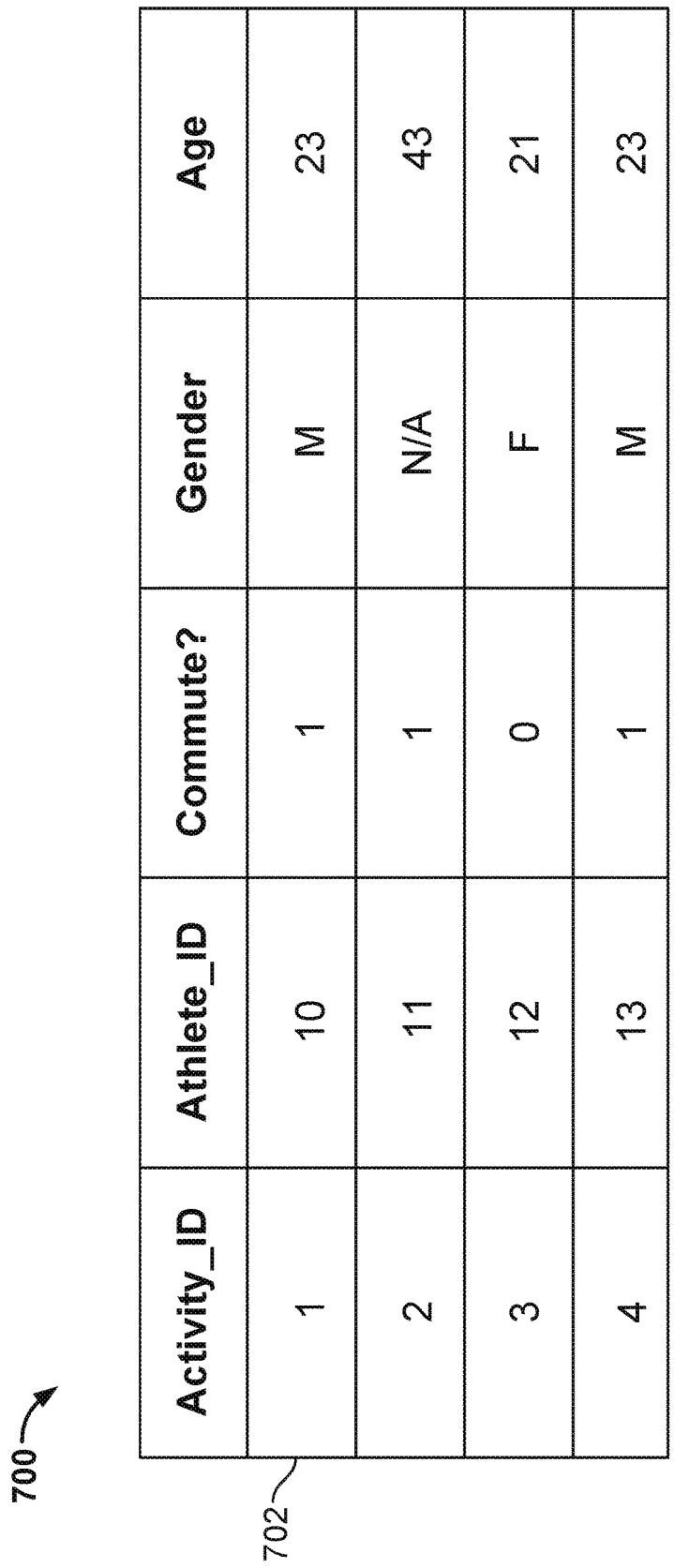
FIG. 7 is a diagram showing an example table that is used to store metadata associated with user activities that match an edge and are associated with one particular preset time interval in a preset period in accordance with some embodiments.

At 406, a subset of the plurality of user activities that matches an edge of the base map is determined. In various embodiments, which user activities (of the activity type associated with the user preference map) have fully traversed an edge in the base map are determined using a set of matching criteria. In some embodiments, the set of matching criteria that is used to determine whether a user activity matches an edge is configured by an administrator. FIG. 7, below, describes an example of using a set of matching criteria to determine whether a user activity matches an edge.

At 408, metadata associated with the subset of the plurality of user activities that matches the edge in a user preference map is stored in a user preference map. In various embodiments, a user preference map (associated with an activity type) is generated by writing metadata of the user activities that match each edge in the obtained base map. In various embodiments, the metadata associated with the user activities that match the edge includes the number of user activities that matched the edge, the data that was recorded (e.g., by GPS-enabled devices) for the user activities (e.g., the sets of GPS data and the corresponding auxiliary data), information associated with the user activities (e.g., the identifier associated with the athlete that performed the activity, the activity type associated with the activity, the date and/or period of time during which the activity took place, the device type that was used to record the activity data, and the equipment used by the athlete during the activity), and user activity attributes that were submitted by users associated with the matching user activities (e.g., bike lane quality, road quality, why certain intersections were chosen over others). In various embodiments, the metadata associated with the user activities that match the edge includes the attributes associated with user activities that are described with step 402. In various embodiments, the metadata associated with the user activities that match the edge includes information that was determined from analyzing such user activities. For example, analysis of the user activities may provide a number of times that the edge was traversed in each of both directions, a predicted road surface (e.g., mountain road or paved road) associated with the edge, and a median time that the edge was traversed. As will be described in further detail below, the metadata associated with the user activities that match each edge can be used to determine routes (e.g., spanning one or more edges) of the user preference map that match user inputs associated with route preferences.

Figure 6:
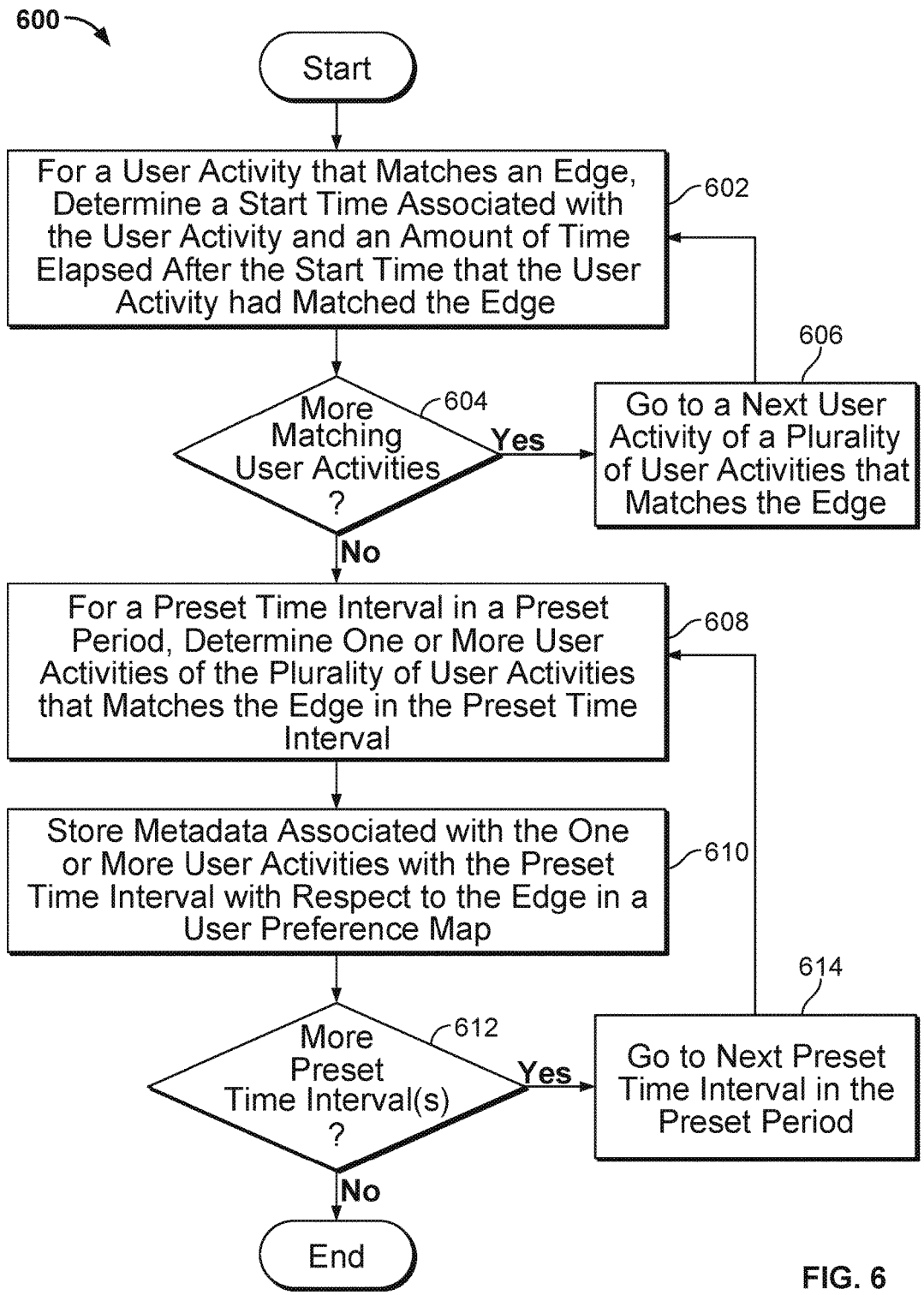
FIG. 6 is a flow diagram showing an example of a process for storing metadata associated with user activities that match an edge per each preset time interval in accordance with some embodiments.

In some embodiments, at least some of the metadata associated with the user activities that match each edge is stored in the user preference map corresponding to associated time intervals. In some embodiments, time intervals, each of a preset length (e.g., one minute time intervals), spanning a preset time period (e.g., the most recent year) can be configured and at least some metadata associated with each user activity that matches the edge and that had been traversing the edge during one or more time intervals is stored with each of those corresponding time intervals. As will be described in further detail below, the metadata, organized by time intervals, associated with the user activities that match each edge can be used to determine routes (e.g., spanning one or more edges) of the user preference map that match user inputs associated with route preferences, including a user input time frame. FIGS. 6 and 7, below, describe examples of storing metadata of user activities that match an edge with different corresponding time intervals.

Returning to FIG. 4, at 410, optionally, a set of elevation data associated with the edge is determined based at least in part on the subset of the plurality of user activities that match the edge. In some embodiments, optionally, a set of elevation data describes the elevation profile of the edge. For example, the elevation profile of the edge includes a determined elevation corresponding to each of various points along the route. FIGS. 8 through 10E, below, describe examples of determining elevation data for an edge.

Returning to FIG. 4, at 412, optionally, the set of elevation data is stored with the edge in the user preference map. In some embodiments, if the set of elevation data has been determined for the edge at step 410, then the set of elevation data is stored with the other metadata that was stored with the edge in the user preference map in step 408.

At 414, it is determined whether there is at least one more edge in the base map. In the event that there is at least one more edge in the base map, control is transferred to step 416. Otherwise, in the event that there is not at least one more edge in the base map, control is transferred to step 418.

At 416, a next edge of the base map is selected. Control is then returned to step 406 to determine the metadata to store for the selected next edge of the base map.

In some embodiments, steps 406 through 412 are performed for each edge found in the base map. In some embodiments, steps 406 through 412 are performed for each edge of only a subset of the edges in the base map. Steps 414 and 416 may be used to determine whether there is at least one more edge in the base map and that should be selected for processing using steps 406 through 412.

At 418, optionally, the user preference map is displayed at a user interface. After the user preference map is generated by storing metadata associated with user activities that have been determined to match each edge in the base map, the metadata stored with each edge in the base map can be visualized and presented on a map at a user interface. For example, at least one attribute from the metadata stored with each edge in the user preference map can be visualized and displayed on the map. For example, the number of user activities that was determined to match each edge may be considered as a degree of popularity associated with that edge. The popularities of different edges may be visualized and displayed at the map in a manner such that the relative popularities of the edges can be presented. For example, the more popular edges may be displayed in a different opacity or a different color than less popular edges.

Figure 5:
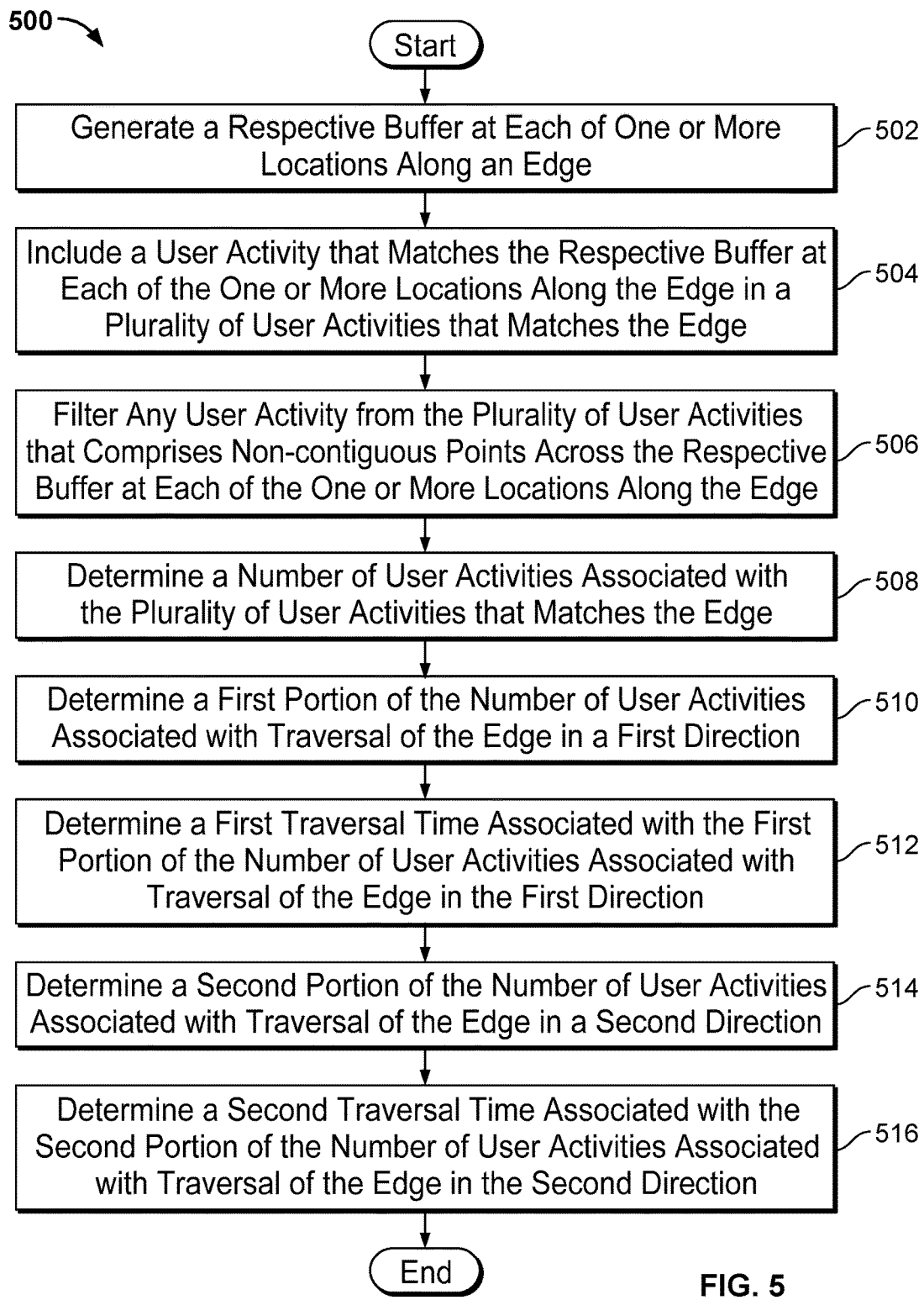
FIG. 5 is a flow diagram showing an example of a process for determining and analyzing user activities that match an edge in accordance with some embodiments.

FIG. 5 is a flow diagram showing an example of a process for determining and analyzing user activities that match an edge in accordance with some embodiments. In some embodiments, process 500 is implemented at system 100 of FIG. 1. In some embodiments, process 500 may be used to implement step 406, at least in part, of process 400 of FIG. 4.

Process 500 is an example process that shows determining a user activity that meets one or more matching criteria associated with an edge of a base map that matches that edge. In some embodiments, a user activity that is determined to match an edge is a user activity that has fully traversed the edge from one endpoint of the edge to the other endpoint of the edge. Process 500 is also an example process that describes analyzing the user activities that have been determined to match the edge.

At 502, a respective buffer is generated at each of one or more locations along an edge. For example, a 20 meter buffer is generated at each of the start, middle, and end points of the edge. The start and end endpoints of the edge may be initially arbitrarily designated but the designations will remain consistent throughout process 500. Generally, recorded GPS data points associated with a user activity are almost never directly on a road, path, or trail, they all drift a few inches to a few meters. However, in some embodiments, recorded GPS data points that are beyond the generated buffer from the edge are ignored.

At 504, a user activity that matches the respective buffer at each of the one or more locations along the edge is included in a plurality of user activities that matches the edge. In some embodiments, a matching criterion for an edge is that the recorded GPS data points associated with a user activity should be present at each of the three buffered locations (e.g., start, middle, end) of the edge. For example, the mined user activities are queried for user activities that are present in each of the start, middle, and buffered locations of the edge. Put another way, user activities whose corresponding GPS data indicates presence in each of the start, middle, and end buffered locations of the edge are determined. The user activities for which recorded GPS data is present in each of the three buffered edge locations are considered to have crossed/traversed the entire edge.

At 506, any user activity from the plurality of user activities that comprises non-contiguous points across the respective buffer at each of the one or more locations along the edge is filtered. In some embodiments, another matching criterion for an edge is that the recorded GPS data points associated with a user activity that are present at each of the three buffered locations (e.g., start, middle, end) of the edge cannot be non-contiguous. As such, any user activity that is associated with non-contiguous GPS data points across the three buffered edge locations may be removed from the set of user activities that have been determined to match the edge. Filtering out user activities with non-contiguous GPS data points ensures that the GPS data points from user activities present were all recorded contiguously and not from different parts of the same ride or run. This ensures that each matching user activity actually crossed the edge from one end to the other.

At 508, a number of user activities associated with the plurality of user activities that matches the edge is determined. The total number of user activities that has been determined to match the edge is determined.

In some embodiments, an equipment type associated with each matching user activity is determined and used to infer the surface type associated with the edge. For example, if user activities were associated with cycling, then the frame type (e.g., mountain bike frame type or road bike frame type) of each matching user activity can be determined. If there are more mountain bike frame type matching user activities, then the surface type of the edge may be inferred to be unpaved and if there are more road bike frame type matching user activities, then the surface type of the edge may be inferred to be paved. The inferred surface type associated with the edge may be stored with the edge in the user preference map, in some embodiments.

At 510, a first portion of the number of user activities associated with traversal of the edge in a first direction is determined. A direction associated with a user activity's traversal across the edge can be determined by comparing the recorded timestamp associated with the user activity's recorded GPS data point that is closest to the designated start endpoint of the edge to the recorded timestamp associated with the user activity's recorded GPS data point that is closest to the designated end endpoint of the edge. If the user activity's recorded timestamp near the designated start of the edge is earlier than the recorded timestamp near the designated end of the edge, then the user activity is determined to have traversed the edge from the designated start of the edge to the designated end. Otherwise, if the user activity's recorded timestamp near the designated start of the edge is later than the recorded timestamp near the designated end of the edge, then the user activity is determined to have traversed the edge from the designated end of the edge to the designated start. A number of the user activities that match the edge that are determined to have traversed the edge in a first direction (e.g., from the designated start to designated end of the edge) is determined.

At 512, a first traversal time associated with the first portion of the number of user activities associated with traversal of the edge in the first direction is determined. Average traversal times are tricky here because sometimes users stop for an hour in the middle of an edge which throws averages off. In some embodiments, a median traversal time (e.g., a duration of the user activity associated with a traversal of the edge) among the user activities that were determined to have traversed the edge in the first direction is determined. This median traversal time represents an average time it takes to traverse the edge in the first direction.

At 514, a second portion of the number of user activities associated with traversal of the edge in a second direction is determined. A number of the user activities that match the edge that are determined to have traversed the edge in a second, opposite direction (e.g., from the designated end to designated start of the edge) is also determined.

At 516, a second traversal time associated with the second portion of the number of user activities associated with traversal of the edge in the second direction is determined. In some embodiments, a median traversal time (e.g., a duration of the user activity associated with a traversal of the edge) among the user activities that were determined to have traversed the edge in the second direction is determined. This median traversal time represents an average time it takes to traverse the edge in the second direction.

In some embodiments, the median traversal time in each direction can be compared against each other to infer a general elevation profile associated with the edge. For example, if the median traversal time in a first direction is longer than the median traversal time in a second direction, then it can be inferred that traversing the edge in the first direction includes more uphill climbing than traversing the edge in the second direction. In some embodiments, the number of traversals in each direction of the edge, the median traversal times in each direction of the edge, and/or an inferred elevation profile of the edge is stored with the edge in the user preference map.

FIG. 6 is a flow diagram showing an example of a process for storing metadata associated with user activities that match an edge per each preset time interval in accordance with some embodiments. In some embodiments, process 600 is implemented at system 100 of FIG. 1. In some embodiments, process 600 may be used to implement step 408, at least in part, of process 400 of FIG. 4.

Process 600 is an example process used to determine which user activities that match an edge are associated with traversing the edge during each time interval (of a preset length) during a preset period. In some embodiments, the preset length of each time interval and the preset period is configured by a system administrator. For example, each preset time interval is one minute long and the preset period is the past year (e.g., the most recent 365 days). For example, if the past year spanned from Jan. 1, 2014 through Dec. 31, 2014, then the first preset time interval of that preset period would span Jan. 1, 2014 at 12:00 am to Jan. 1, 2014 at 12:01 am, and the second preset time interval of that preset period would span Jan. 1, 2014 at 12:01 am to Jan. 1, 2014 at 12:02 am, and so on, and the last preset time interval of that preset period would span Dec. 31, 2014 at 11:58 pm to Dec. 31, 2014 at 11:59 pm.

At 602, for a user activity that matches an edge, a start time associated with the user activity and an amount of time elapsed after the start time that the user activity had matched the edge is determined. In process 600, it is assumed that the user activities that match the edge have already been determined (e.g., by a process such as process 500 of FIG. 5). Each such matching user activity is considered to see the start time recorded for the user activity (e.g., the start time is the recorded time at which the user activity had begun) and an amount of time (e.g., a number of seconds) into the user activity before the user activity had matched the edge. For example, matching the edge includes when the recorded GPS data points associated with the user activity indicated that the user activity that started to traverse the locations of the edge. For example, assume that the recorded start time for a matching user activity was Sep. 21, 2014 at 1:00 pm and it is determined that at Sep. 21, 2014 at 1:34 pm, the user activity actually started to traverse the edge. In some embodiments, an amount of time elapsed after the start time of the user activity before the user activity had completed the edge (e.g., was no longer traversing along the edge) can also be determined. The start time of the matching user activity and the amount of time elapsed after the start time that the user activity matched the edge are used to determine the times during which the matching user activity had actually traversed the edge.

At 604, it is determined whether there is at least one more user activity among the plurality of user activities that matches the edge. In the event that there is at least one more matching user activity, control is transferred to step 606, where the next user activity is addressed. Otherwise, in the event there is not at least one more matching user activity, control is transferred to 608.

At 608, for a preset time interval during a preset period, one or more user activities of the plurality of user activities that matches the edge in the preset time interval are determined. To determine which of the matching user activities matches the edge in a preset time interval, it is determined whether the duration of which a user activity matches the edge, as determined above at 602, includes the preset time interval. For example, if the current preset time interval spanned the minute between Nov. 26, 2014 9:10 am to Nov. 26, 2014 9:11 am, then a first user activity that traversed the edge between Nov. 26, 2014 8:29 am to Nov. 26, 2014 11:23 am would matched the edge in that preset time interval but a second user activity that traversed the edge between Nov. 26, 2014 1:03 pm to Nov. 26, 2014 3:45 pm would not match the edge in that preset time interval.

At 610, metadata associated with the one or more user activities is stored with the preset time interval with respect to the edge in a user preference map. The metadata associated with those user activities that match the edge and have been determined to match the edge in the preset time interval is stored, for example, in a data structure or table associated with that preset time interval associated with the edge in the user preference map. As such, for an edge, a data structure or table may be used to store the metadata associated with the one or more user activities associated with each corresponding preset time interval in the preset period. FIG. 7, below, shows an example of such a table corresponding to a particular preset time interval for an edge.

Returning to FIG. 6, at 612, it is determined whether there is at least one more preset time interval in the preset period. In the event that there is at least one more preset time interval in the preset period, control is transferred to step 614, where the next preset time interval is addressed. Otherwise, in the event there is not at least one more preset time interval in the preset period, process 600 ends. Until the last preset time interval of the preset period is reached, steps 608 through 614 are repeated for each subsequent preset time interval.

FIG. 7 is a diagram showing an example table that is used to store metadata associated with user activities that match an edge and are associated with one particular preset time interval in a preset period in accordance with some embodiments. Table 700 stores the metadata associated with four user activities that match an edge with respect to one particular preset time interval. Each row of table 700 stores a set of metadata associated with one user activity that was determined to match the edge with respect to the particular preset time interval. In the example of table 700, the set of metadata associated with each user activity includes "Activity_ID" (an identifier of the user activity), "Athlete_ID" (an identifier of the user associated with the activity), "Commute?" (an indication of whether the activity took place during a commute time frame), "Gender" (a gender of the user associated with the activity, if available), and "Age" (an age of the user associated with the activity). For example, metadata at row 702 associated with a user activity is associated with an activity identifier of 1, an athlete identifier of 10, an indication that it took place during a commute time frame, a gender of male, and an age of 23 years. A table similar to table 700 may be stored for each preset time interval in the preset period, and for each edge in a user preference map.

Figure 8:
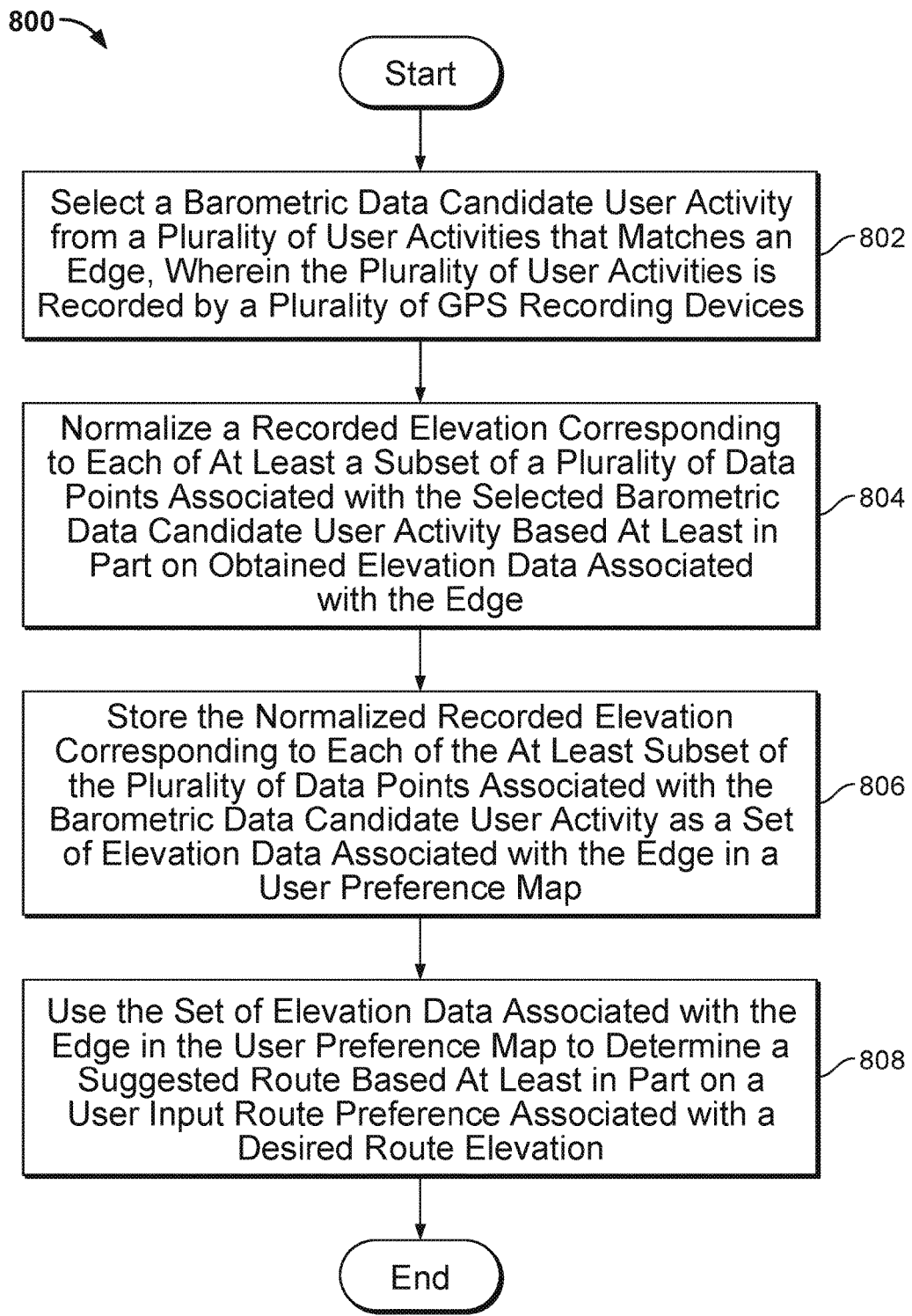
FIG. 8 is a flow diagram showing a process for determining a set of elevation data associated with an edge in accordance with some embodiments.

FIG. 8 is a flow diagram showing a process for determining a set of elevation data associated with an edge in accordance with some embodiments. In some embodiments, process 800 is implemented at system 100 of FIG. 1. In some embodiments, process 800 is used to implement step 410, at least in part, of process 400 of FIG. 4.

At 802, a barometric data candidate user activity is selected from a plurality of user activities that matches an edge, wherein the plurality of user activities is recorded by a plurality of GPS recording devices. A user activity of the set of user activities that has been determined to match the edge is selected and referred to as the selected "barometric data candidate user activity."

At 804, a recorded elevation corresponding to each of at least a subset of a plurality of data points associated with the barometric data candidate user activity is normalized based at least in part on obtained elevation data associated with the edge. In various embodiments, existing elevation data associated with the edge is looked up from a third party source (e.g., USGS). The recorded elevation corresponding to each GPS data point of the selected barometric data candidate user activity is normalized based at least in part on the looked up elevation data to determine the set of elevation data for the edge.

At 806, the normalized recorded elevation corresponding to each of the at least subset of the plurality of data points associated with the barometric data candidate user activity is stored as a set of elevation data associated with the edge in a user preference map. In some embodiments, the set of elevation data determined for the edge is stored with the edge in a user preference map. The set of elevation data determined for the edge describes an elevation profile of the edge. In various embodiments, the user preference map can be determined as described above.

At 808, the set of elevation data associated with the edge in the user preference map is used to determine a suggested route based at least in part on a user input route preference associated with a desired route elevation. The set of elevation data stored with the edge in the user preference map may be used to assist in routing. In particular, when a user input route preference is associated with a desired route elevation, the set of elevation data stored with the edge in the user preference map can be used to determine whether the edge should be included as part of a suggested route (e.g., in between a user input start endpoint and a user input end endpoint). For example, a desired route elevation may be associated with a desired average elevation of a route, a desired maximum elevation in a route, or a desired minimum elevation in a route.

In various embodiments, two data sources of elevation data associated with an edge are available and when used in conjunction, the combined data yields a highly accurate elevation profile aggregated to each edge in a user preference map.

In some embodiments, the first data source for elevation data is a resource such as the USGS (United States Geologic Survey), which is compiled using various techniques. This looked up type of elevation data provides enough absolute accuracy. "Absolute accuracy" describes that the looked up elevation values provided are close to the correct numbers and accurate enough for the purpose this process uses them for. This looked up type of elevation data is, however, not accurate enough for the purpose of looking up an elevation profile for an edge.

In some embodiments, the second data source for elevation data is barometric data as collected by various GPS recording devices in association with recorded user activities. For example, the Garmin Edge 305, 500, 800 and 1000 series as well as some of the newer mobile phones such as the iPhone 6 series, collect barometric data in addition to corresponding GPS data. Elevation data as captured by these devices is highly accurate in a relative sense, meaning that the difference in the recorded elevation value corresponding to one GPS data point and the recorded elevation value corresponding to an immediately successive GPS data point is highly accurate. However, this recorded type of elevation data is not accurate in an absolute sense. The same device may record elevation values on the same street from one day to the next that have identical profiles, but are offset by tens of meters making them relatively very accurate, but absolutely inaccurate.

In various embodiments, the two types of elevation data, the looked up elevation data and the recorded user activity barometric data is used together to determine a set of elevation data that describes an elevation profile of each edge in a user preference map. The absolute looked up elevation from the USGS and such are used to "anchor" the relatively accurate barometric elevation, thereby making the barometric elevation data both absolutely and relatively accurate. This data is then aggregated to the edges (e.g., roads, paths, and trails) on which is recorded for future looking for routing, and elevation correction of activities that traverse it, for example.

Figure 9:
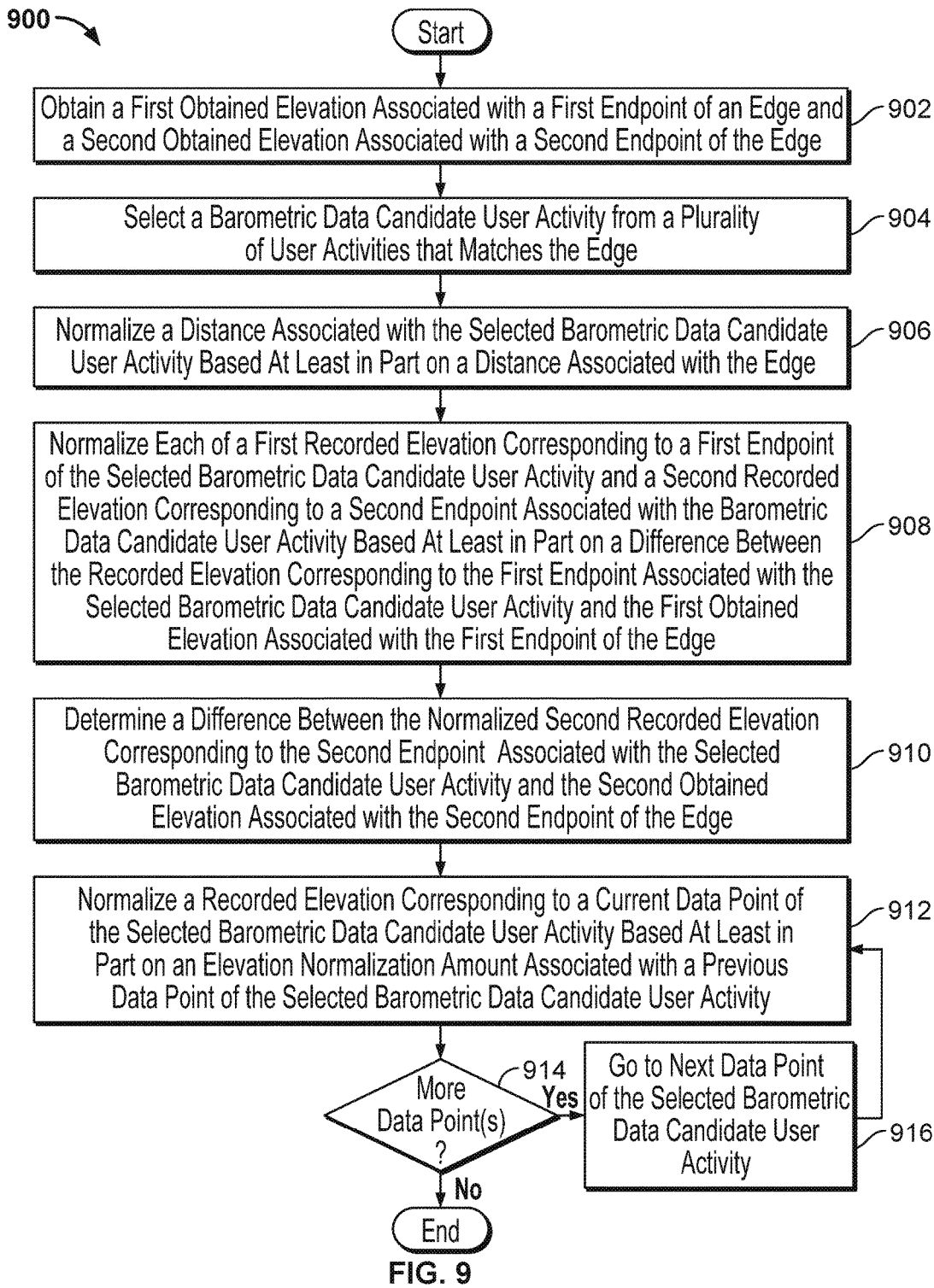
FIG. 9 is a flow diagram showing an example of a process for determining a set of elevation data associated with an edge in accordance with some embodiments.

FIG. 9 is a flow diagram showing an example of a process for determining a set of elevation data associated with an edge in accordance with some embodiments. In some embodiments, process 900 is implemented at system 100 of FIG. 1. In some embodiments, process 900 is used to implement process 800, at least in part, of FIG. 8.

At 902, a first obtained elevation associated with a first endpoint of an edge is obtained and a second obtained elevation associated with a second endpoint of the edge is obtained. The elevation of the start of the edge and the elevation of the end of the edge is looked up via the server of USGS or the server of a similar elevation source. The start and end points of the edge may be initially arbitrarily designated but the designations will remain consistent through process 900.

At 904, a barometric data candidate user activity is selected from a plurality of user activities that matches the edge. In process 900, it is assumed that the user activities that match the edge have already been determined (e.g., by a process such as process 500 of FIG. 5). It is possible that fewer than all the matching user activities are recorded with barometric data (e.g., depending on the availability of a barometric altimeter function on the corresponding GPS recording devices). Of the matching user activities that are recorded with barometric data, one of such user activities is selected to act as a reference user activity whose corresponding recorded set of GPS data will be normalized and then stored as the set of elevation data associated with the edge. This reference user activity is referred to as the selected "barometric data candidate user activity."

In some embodiments, to select the barometric data candidate user activity, first, the difference between the looked up edge start elevation and the looked up end elevation is calculated. For example, assume that an edge has a looked up start elevation of 100 meters (m) and a looked up end elevation of 110 m. The difference between the looked up edge start elevation and the looked up end elevation of the edge in this example would be 10 m. Each of the user activities that have been determined to match the edge and is recorded with barometric data is obtained. The difference between the recorded start elevation (e.g., the recorded elevation corresponding to the GPS data point of the user activity that is closest to the start of the edge) and the recorded end elevation (e.g., the recorded elevation corresponding to the GPS data point of the user activity that is closest to the end of the edge) of each such user activity is determined. Each of such user activity is given a ranking based on how close the difference of the user activity's recorded start and end elevations is compared to the calculated difference between the looked up edge start elevation and the looked up end elevation of the edge. For example, the best candidate user activity is the one with the closest difference and is therefore the user activity with the highest ranking. For example, the best candidate user activity is selected to be the "barometric data candidate user activity."

In some embodiments, the selected barometric data candidate user activity will be processed based on 906 through 916 but if the selected barometric data candidate user activity meets one or more ignore conditions, then the current selected barometric data candidate user activity is ignored and replaced with the next highest ranking user activity of the ranked list. A first example of an ignore condition is if during the process, a max grade within the normalized recorded elevation exceeds a 40% grade, the selected barometric data candidate user activity is ignored and the next highest ranking user activity is considered and tested. A second example of an ignore condition is if there is a recording gap of greater than 40 m or 1 minute between two GPS data points of the selected barometric data candidate user activity, then the selected barometric data candidate user activity is ignored and the next highest ranking user activity is considered and tested. Barometric pressure can change rapidly, creating the possibility of large apparent elevation changes if too much time passes between recorded GPS data points. Normally a time gap means the recorded user activity paused part way through an edge before resuming. However, this process requires seamless and consistent data.

At 906, a distance associated with the selected barometric data candidate user activity is normalized based at least in part on a distance associated with the edge. The distance of the selected barometric data candidate user activity from where it matched the start and the end of the edge needs to be normalized to match the distance of the edge so the GPS data points along the edge where the normalized elevation data will be placed correspond exactly to the places on the edge where the elevations should be placed.

For example, if the edge is 100 meters long, and the selected barometric data candidate user activity is 104 meters long, then those 104 meters need to be compressed to fit the 100 meters of the edge. In this example, the distance interval between GPS data points of the selected barometric data candidate user activity needs to be set to 96.15% of the recorded distance making the sum of the recorded distance equal to exactly 100 meters, the same as the length of the edge.

At 908, each of a first recorded elevation corresponding to a first endpoint of the selected barometric data candidate user activity and a second recorded elevation corresponding to a second endpoint associated with the barometric data candidate user activity are normalized based at least in part on a difference between the recorded elevation corresponding to the first endpoint associated with the barometric data candidate user activity and the first obtained elevation associated with the first endpoint of the edge. In various embodiments, the recorded elevation data of the selected barometric data candidate user activity that matched the start and end of the edge is normalized to match the looked up elevation of the start and end of the edge to ensure a seamless and smooth elevation profile for the edge.

The first step in normalizing the elevation data of the selected barometric data candidate user activity is to normalize the recorded start elevation of the selected barometric data candidate user activity to the same value as the looked up start elevation of the edge. The amount the recorded start elevation of the selected barometric data candidate user activity is normalized becomes the baseline with which to normalize the recorded elevation corresponding to each subsequent GPS data point of the selected barometric data candidate user activity such that the normalized end elevation of the selected barometric data candidate user activity becomes equal to the looked up end elevation of the edge.

At 910, a difference between the normalized second recorded elevation corresponding to the second endpoint associated with the selected barometric data candidate user activity and the second obtained elevation associated with the second endpoint of the edge is determined. The difference between the normalized recorded end elevation of the selected barometric data candidate user activity and the looked up end elevation of the edge is determined.

For example, if the edge has a looked up start elevation of 100 m and a looked up end elevation of 110 m and the selected barometric data candidate user activity has a recorded start barometric elevation of 120 m and a recorded end barometric elevation of 132 m, the first step is to reduce both of the recorded start barometric elevation and the recorded end barometric elevation by 20 m (the difference between the recorded start barometric elevation of 120 m and the looked up start elevation of 100 m, thereby making the normalized recorded elevations 100 m and 112 m, respectively). This makes the recorded start elevation of the selected barometric data candidate user activity the same as the looked up start elevation of the edge, and the normalized recorded end elevation of the selected barometric data candidate user activity 2 m higher than the looked up end elevation of the edge.

At 912, a recorded elevation corresponding to a current data point of the selected barometric data candidate user activity is normalized based at least in part on an elevation normalization amount associated with a previous data point of the selected barometric data candidate user activity. In various embodiments, each GPS data point of the selected barometric data candidate user activity is iterated through and the corresponding recorded elevation of each current GPS data point is normalized based at least in part on the normalization amount applied to the previous GPS data point of the selected barometric data candidate user activity. In some embodiments, the recorded elevation of each current GPS data point is normalized as a function of the normalization amount applied to the previous GPS data point of the selected barometric data candidate user activity, the interval distance between the current GPS data point and the previous GPS data point relative to the distance of the edge, and the difference between the normalized recorded end elevation of the selected barometric data candidate user activity and the looked up end elevation of the edge. For example, the recorded elevation for the current GPS data point is normalized by the normalization amount applied to the previous GPS data point in addition to an amount determined by multiplying the percentage of the distance of the interval between the current GPS data point and the previous GPS data point of the selected barometric data candidate user activity to the total edge distance and the difference between the normalized recorded end elevation of the selected barometric data candidate user activity and the looked up end elevation of the edge.

Returning to the example described with step 912, the difference between the normalized recorded end elevation value and the looked up end value of the edge is 2 m. The distance of the edge is 100 m. If the current recorded GPS data point, which is the GPS data point that is immediately subsequent to the recorded GPS data point at the start of the edge, is 5 m from the previous GPS data point at the start of the edge (the interval distance between the current GPS data point and the previous GPS data point is 5% of the edge distance), the product of 5% and the total elevation difference between the normalized recorded end elevation value and the looked up end value of the edge (i.e., 2 m) is 0.1 m. Since the normalization amount of the recorded elevation of the previous data was 10 m, then the recorded elevation corresponding to the current GPS data point would be (10+0.1=) 10.1 m. Thus, the recorded elevation corresponding to the current GPS data point is normalized by subtracting 10.1 m from the original recorded elevation value corresponding to the current GPS data point.

FIGS. 10A through 10D, below, describe an example of normalizing the recorded elevation of each subsequent GPS data point in a selected barometric data candidate user activity.

Returning to FIG. 9, at 914, it is determined whether there is at least one more data point in the selected barometric data candidate user activity. In the event that there is at least one more GPS data point in the selected barometric data candidate user activity, control is transferred to step 916. Otherwise, in the event that there is not at least one more GPS data point in the selected barometric data candidate user activity, process 900 ends.

At 916, a next data point of the selected barometric data candidate user activity is selected. Control is returned to step 912 to continue normalization on the recorded elevation for this subsequent GPS data point of the selected barometric data candidate user activity.

After applying process 900, the normalized recorded end elevation of the selected barometric data candidate user activity should be adjusted to match the looked up end elevation of the edge. The normalized set of elevations corresponding to the respective GPS data points of the selected barometric data candidate user activity can be used as the set of elevation data associated with the edge. In some embodiments, the normalized set of elevations corresponding to the respective GPS data points of the selected barometric data candidate user activity is stored as the set of elevation data associated with the edge in the user preference map.

FIGS. 10A through 10E show an example of normalizing the elevation data associated with a selected barometric data candidate user activity to serve as the set of elevation data for an edge. As will be illustrated with FIGS. 10A through 10E, the amount that the recorded elevation of each GPS data point of the selected barometric data candidate user activity is normalized carries to the next GPS data point. As such, by the time that the recorded elevation corresponding to the last GPS data point (e.g., the GPS data point at the end of the edge) is to be normalized, its recorded elevation can be normalized by an amount that will equal to the difference between the looked up end elevation of the edge and the original recorded end elevation.

Figure 10A:
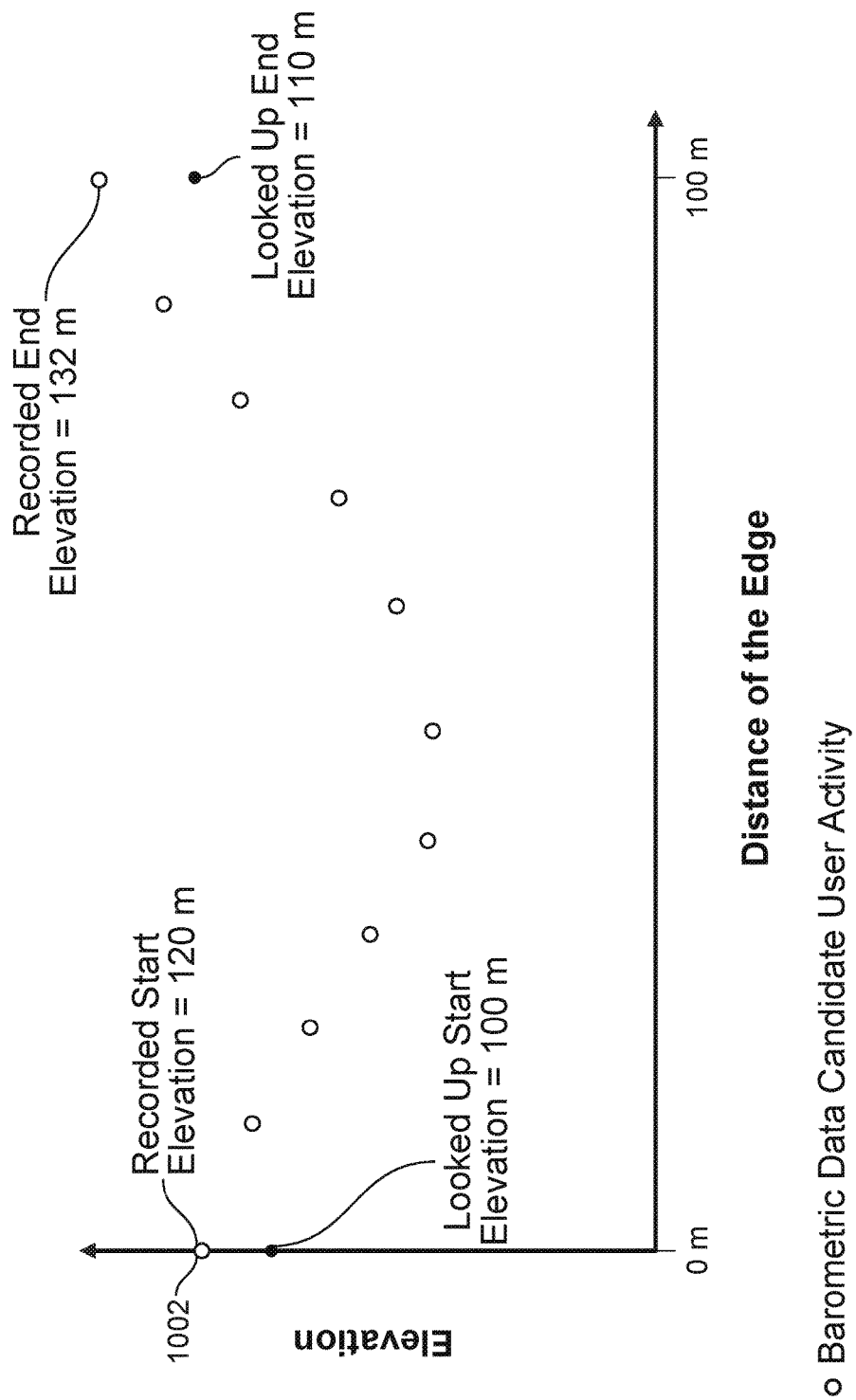
FIG. 10A is a diagram showing an example of recorded and looked up elevation data associated with an edge in accordance with some embodiments.

FIG. 10A is a diagram showing an example of recorded and looked up elevation data associated with an edge in accordance with some embodiments. In the example of FIG. 10A, the edge is 100 m and a barometric data candidate user activity has already been selected for the edge. There are 11 GPS data points recorded for the selected barometric data candidate user activity that span the start and end of the edge. The elevation recorded for each of the 11 recorded GPS data points is represented by a small white circle in the diagram, such as circle 1002. The distance of the selected barometric data candidate user activity may have already been normalized to match the distance of the edge. As shown in the example, the looked up start elevation of the edge is 100 m, the looked up end elevation of the edge is 110 m, the recorded elevation of the first GPS data point of the selected barometric data candidate user activity at the start of the edge (the "recorded start elevation") is 120 m, and the recorded elevation of the last GPS data point of the selected barometric data candidate user activity at the end of the edge (the "recorded end elevation") is 132 m. As described with step 908 of process 900 of FIG. 9, each of the recorded start elevation and recorded end elevation of the selected barometric data candidate user activity is to be normalized by the difference between the recorded start elevation (120 m) and the looked up start elevation (100 m), which is 20 m.

Figure 10B:
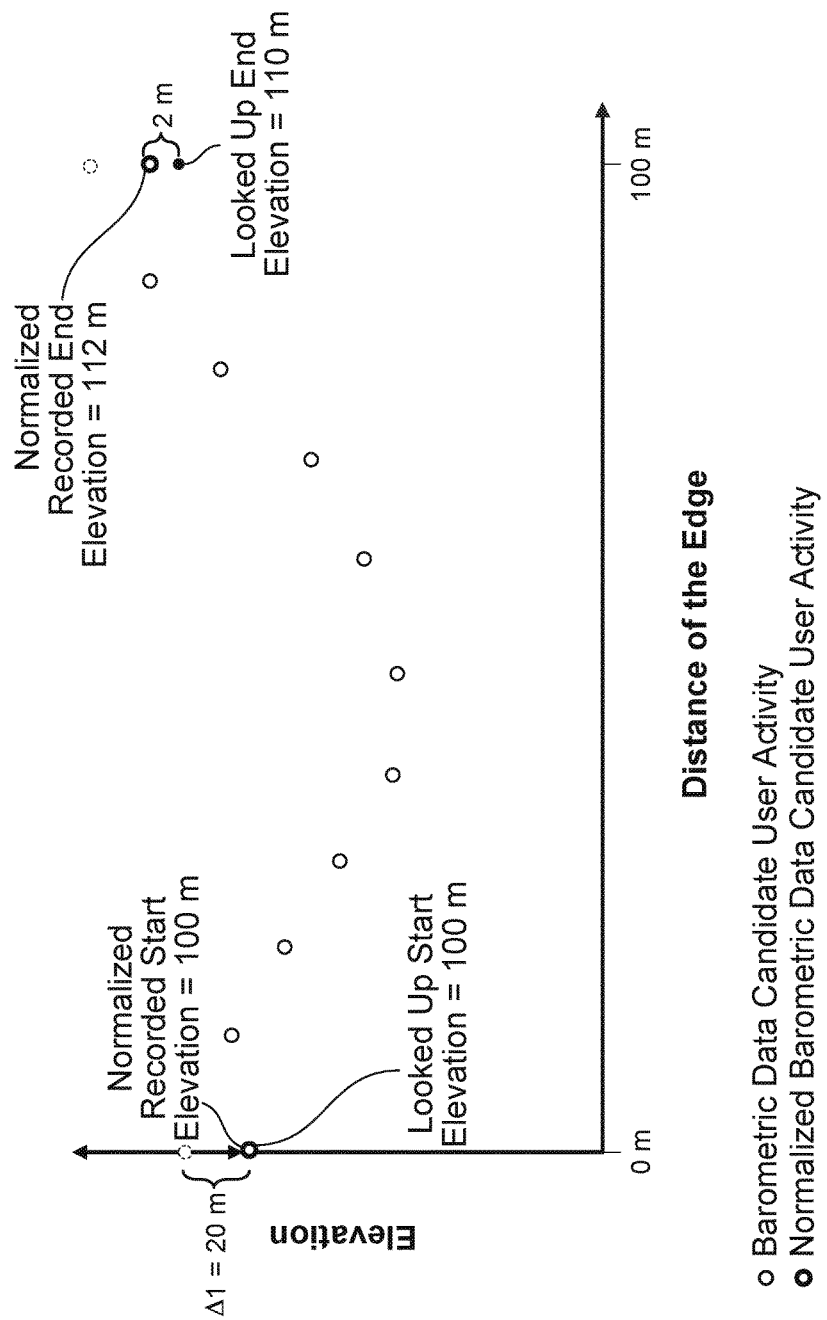
FIG. 10B is a diagram showing an example of normalizing the recorded start barometric elevation and the recorded end barometric elevation of a barometric data candidate user activity that was selected for an edge in accordance with some embodiments.

FIG. 10B is a diagram showing an example of normalizing the recorded start barometric elevation and the recorded end barometric elevation of a barometric data candidate user activity that was selected for an edge in accordance with some embodiments. To continue the example of FIG. 10A, after each of the recorded start elevation and recorded end elevation of the selected barometric data candidate user activity is normalized (reduced) by 20 m, the normalized recorded start elevation and the normalized recorded end elevation of the selected barometric data candidate user activity are now 100 m and 112 m, respectively. The normalization amount for the normalized recorded start elevation corresponding to the GPS data point of the selected barometric data candidate user activity at the start of the edge, $\Delta 1$, is 20 m. While the normalized recorded start elevation of 100 m now matches the looked up start elevation of 100 m, the normalized recorded end elevation of 112 m is still 2 m greater than the looked up end elevation of 110 m. As such, the recorded elevation of each GPS data point of the selected barometric data candidate user activity subsequent to the first GPS data point at the start of the edge, including the originally recorded end elevation corresponding to the GPS data point associated with the end of the edge, is iteratively normalized/adjusted such that the normalized recorded end elevation will match the looked up end elevation.

Figure 10C:
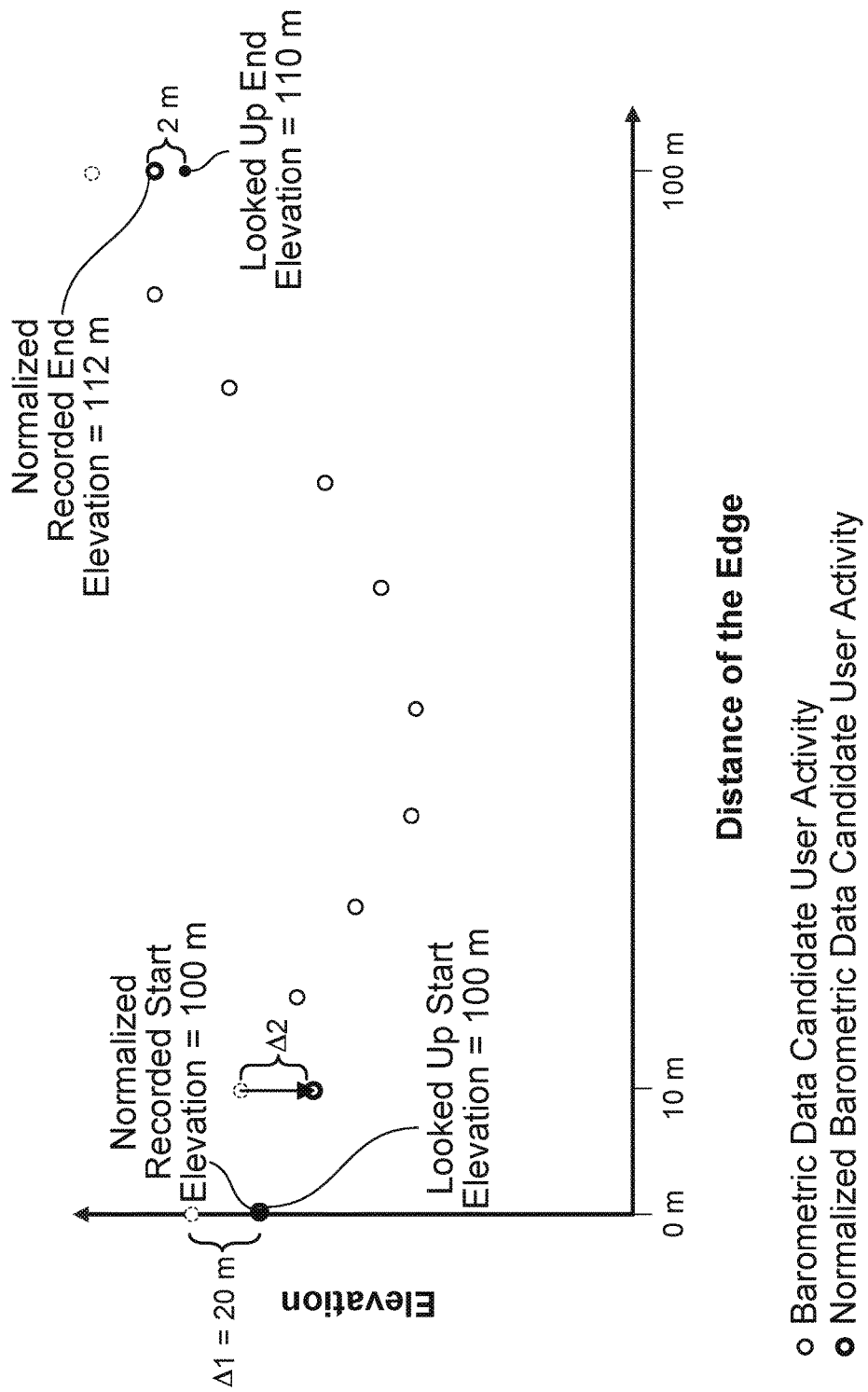
FIG. 10C is a diagram showing an example of normalizing the recorded barometric elevation corresponding to a second GPS data point of the selected barometric data candidate user activity in accordance with some embodiments.

FIG. 10C is a diagram showing an example of normalizing the recorded barometric elevation corresponding to a second GPS data point of the selected barometric data candidate user activity in accordance with some embodiments. To continue the example of FIG. 10B, the recorded elevation corresponding to the GPS data point of the selected barometric data candidate user activity recorded immediately after the GPS data point at the start of the edge (the second GPS data point of the selected barometric data candidate user activity) is to be normalized next. As shown in the diagram, the interval distance between the previous GPS data point, which is at 0 m relative to the start of the edge, and the current GPS data point, which is at 10 m relative to the start of the edge, is 10 m. As described with step 910 of process 900 of FIG. 9, the recorded elevation of the current GPS data point is normalized as a function of the normalization amount applied to the previous GPS data point of the selected barometric data candidate user activity, the interval distance between the current GPS data point and the previous GPS data point relative to the distance of the edge, and the difference between the normalized recorded end elevation of the selected barometric data candidate user activity and the looked up end elevation of the edge. In the example of FIG. 10C, the normalization amount applied to the previous GPS data point of the selected barometric data candidate user activity, $\Delta 1$, is 20 m, the interval distance between the current GPS data point and the previous GPS data point relative to the distance of the edge is 10 m, and the difference between the normalized recorded end elevation of the selected barometric data candidate user activity and the looked up end elevation of the edge, as described earlier, is 2 m. As such, the normalization amount to apply to the recorded elevation of the current GPS data point is $\Delta 2 = \Delta 1 + (10/100)*2 = 20 + 0.2 = 20.2$ m. As shown in the diagram, the original recorded elevation corresponding to the current, second GPS data point of the selected barometric data candidate user activity is reduced by $\Delta 2 = 20.2$ m.

Figure 10D:
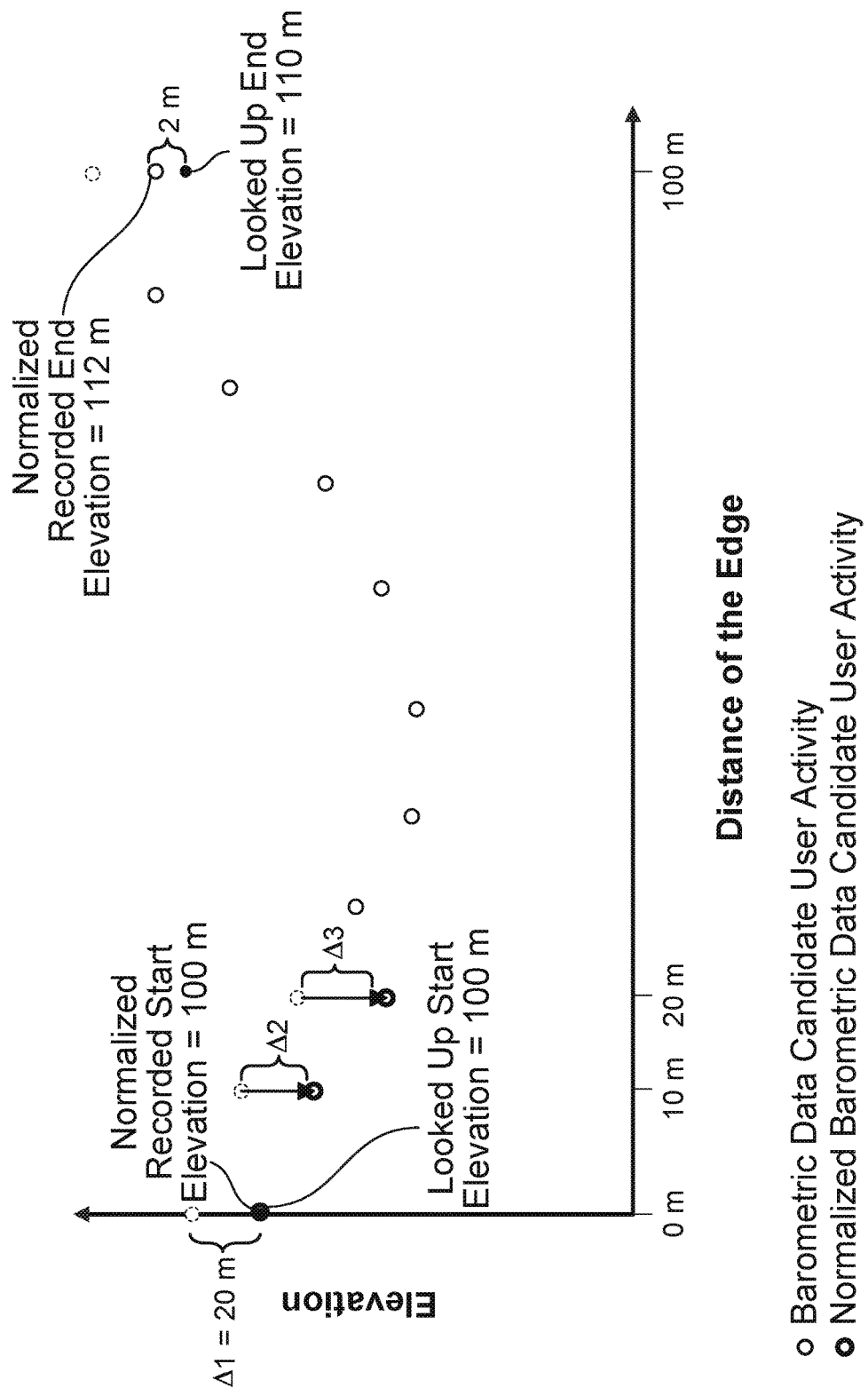
FIG. 10D is a diagram showing an example of normalizing the recorded barometric elevation corresponding to a third GPS data point of the selected barometric data candidate user activity in accordance with some embodiments.

FIG. 10D is a diagram showing an example of normalizing the recorded barometric elevation corresponding to a third GPS data point of the selected barometric data candidate user activity in accordance with some embodiments. To continue the example of FIG. 10C, the recorded elevation corresponding to the third GPS data point of the selected barometric data candidate user activity is to be normalized next. As shown in the diagram, the interval distance between the previous GPS data point, which is at 10 m relative to the start of the edge, and the current GPS data point, which is at 20 m relative to the start of the edge, is 10 m. As described with step 910 of process 900 of FIG. 9 and with the example of FIG. 10C, the recorded elevation of the current GPS data point is normalized as a function of the normalization amount applied to the previous GPS data point of the selected barometric data candidate user activity, the interval distance between the current GPS data point and the previous GPS data point relative to the distance of the edge, and the difference between the normalized recorded end elevation of the selected barometric data candidate user activity and the looked up end elevation of the edge. In the example of FIG. 10D, the normalization amount applied to the previous GPS data point of the selected barometric data candidate user activity, $\Delta 2$, is 20.2 m, the interval distance between the current GPS data point and the previous GPS data point relative to the distance of the edge is 10 m, and the difference between the normalized recorded end elevation of the selected barometric data candidate user activity and the looked up end elevation of the edge, as described earlier, is 2 m. As such, the normalization amount to apply to the recorded elevation of the current GPS data point is $\Delta 3 = \Delta 2 + (10/100)*2 = 20.2 + 0.2 = 20.4$ m. As shown in the diagram, the original recorded elevation corresponding to the current, third GPS data point of the selected barometric data candidate user activity is reduced by $\Delta 3 = 20.4$ m.

Figure 10E:
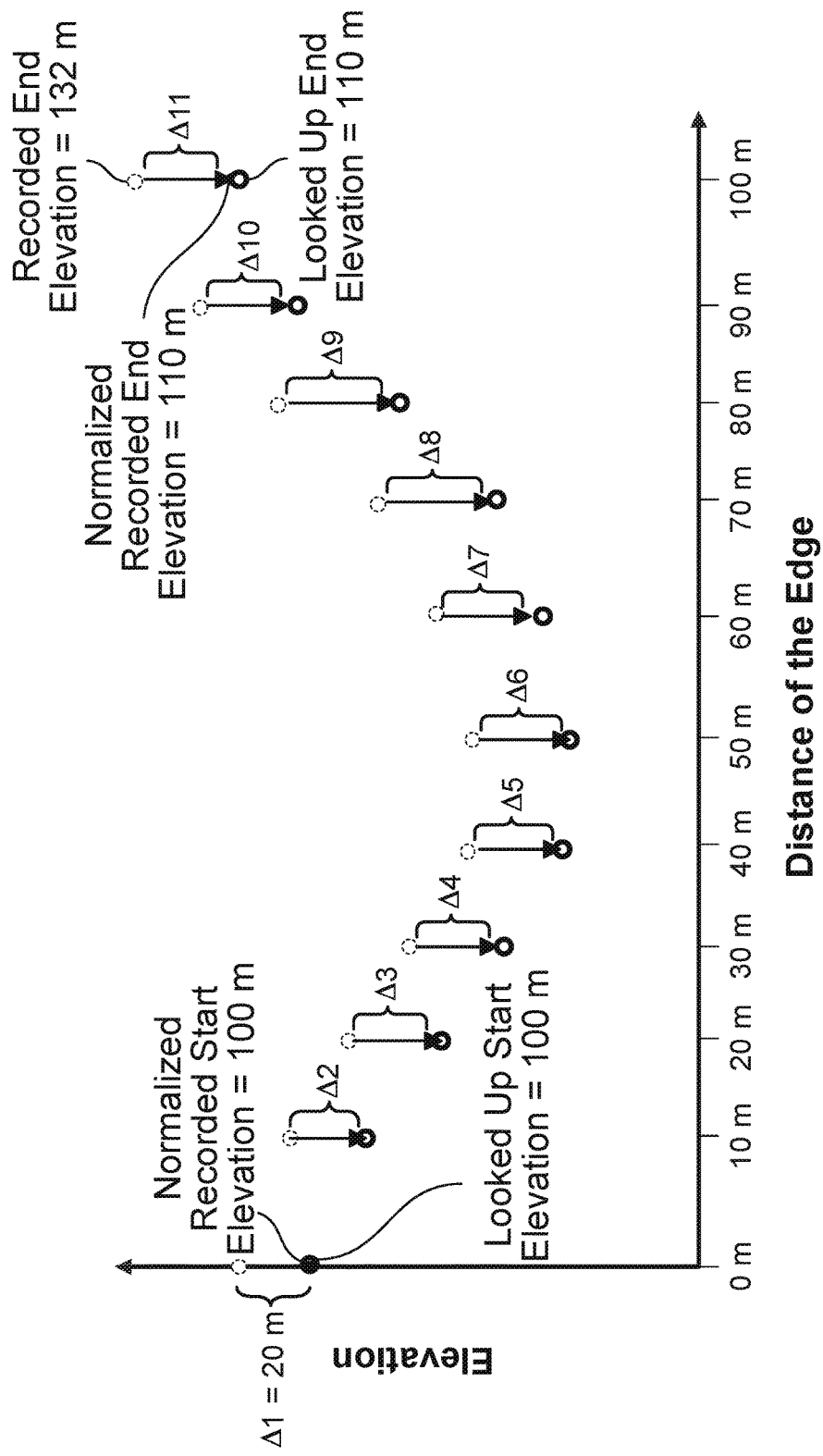
FIG. 10E is a diagram showing an example of normalizing the recorded barometric elevation corresponding to the GPS data point of the selected barometric data candidate user activity at the end of the edge in accordance with some embodiments.

The normalization amounts applied to each of the fourth, fifth, sixth, seventh, eighth, ninth, and tenth GPS data points of the selected barometric data candidate user activity are not shown in FIG. 10D. The interval distance between each subsequent GPS data point and its previous GPS data point in the selected barometric data candidate user activity is 10 m. The respective normalization amounts applied to the fourth, fifth, sixth, seventh, eighth, ninth, and tenth GPS data points of the selected barometric data candidate user activity, which are respectively, $\Delta 4$, $\Delta 5$, $\Delta 6$, $\Delta 7$, $\Delta 8$, $\Delta 9$, and $\Delta 10$, are as follows:

$\Delta 4 = \Delta 3 + (10/100)*2 = 20.4 + 0.2 = 20.6$ m $\Delta 5 = \Delta 4 + (10/100)*2 = 20.6 + 0.2 = 20.8$ m $\Delta 6 = \Delta 5 + (10/100)*2 = 20.8 + 0.2 = 21.0$ m $\Delta 7 = \Delta 6 + (10/100)*2 = 21.0 + 0.2 = 21.2$ m $\Delta 8 = \Delta 7 + (10/100)*2 = 21.2 + 0.2 = 21.4$ m $\Delta 9 = \Delta 8 + (10/100)*2 = 21.4 + 0.2 = 21.6$ m $\Delta 10 = \Delta 9 + (10/100)*2 = 21.6 + 0.2 = 21.8$ m FIG. 10E is a diagram showing an example of normalizing the recorded barometric elevation corresponding to the GPS data point of the selected barometric data candidate user activity at the end of the edge in accordance with some embodiments. To continue the example of FIG. 10D, eventually, after iterating through and applying respective normalization amounts to the fourth, fifth, sixth, seventh, eighth, ninth, and tenth GPS data points of the selected barometric data candidate user activity, the eleventh and last GPS data point of the selected barometric data candidate user activity, the GPS data point at the end of the edge is to be normalized. The normalization amount to be applied to the GPS data point at the end of the edge $\Delta 11$ is determined by $\Delta 11 = \Delta 10 + (10/100)*2 = 21.8 + 0.2 = 22.0$ m. As shown in the diagram, the original recorded end elevation of 132 m (not the previously normalized recorded end elevation of 110 m) corresponding to the current, last GPS data point of the selected barometric data candidate user activity is reduced by $\Delta 11 = 22.0$ m (the difference between the looked up end elevation and the original recorded end elevation) to yield a normalized recorded end elevation of 110 m, which is the same as the looked up end elevation.

As shown in diagrams FIGS. 10A through 10E, as a result of the elevation normalization process, the normalized recorded start and end elevations are adjusted to match the looked up end elevation. The set of normalized recorded elevations corresponding to respective GPS data points of the selected barometric data candidate user activity are stored as the set of elevation data associated with the edge. In various embodiments, the set of elevation data computed for an edge is stored with the edge in a user preference map. The set of normalized recorded elevations corresponding to respective GPS data points of the selected barometric data candidate user activity comprises an accurate elevation profile of the edge and can be used to provide routing suggestions with respect to the edge in response to a user input route preference associated with desired route elevation. In some embodiments, the set of elevation data associated with the edge is stored as a series of absolute elevation values in some embodiments, and the set of elevation data associated with the edge is stored as a series of relative elevation values, where each subsequent elevation value represents a change (e.g., offset) relative to the previous elevation value.

FIG. 11 is a diagram showing an example of a presentation of a user preference map in accordance with some embodiments. The presented user preference map is generated based on aggregated user activity data associated with a particular activity type (e.g., cycling or running). The example of FIG. 11 shows various edges of the base map on which the user preference map was based. As described above, the metadata of user activities that match each edge is stored with each edge in the user preference map. In various embodiments, a user activity that is determined to match an edge is a user activity that is determined to have traversed the edge in its entirety (e.g., from one endpoint of the edge to the other endpoint). A user preference map may be presented by displaying at least some portion of the metadata of user activities that match each edge. In the example of FIG. 11, the user preference map is presented by showing each edge in a greyscale shade that represents the number of matching user activities that was determined to match that edge. In the example of FIG. 11, the darker the greyscale shade of an edge, the greater the number of user activities that was determined to match the edge and therefore, the more popular the edge is. For example, of the three edges 1102, 1104, and 1106 that are presented in the user preference map, edge 1102 is shown in the darkest greyscale shade and is therefore the most popular edge of the three, edge 1104 is shown in the second darkest greyscale shade and is therefore the second most popular of the three, and edge 1106 is shown in the lightest greyscale shade and is therefore the least popular of the three.

The example of FIG. 11 merely shows one example presentation of a user preference map. In some embodiments, the presentation of the user preference map can be adjusted based at least in part on one or more user inputs, as will be described with FIGS. 12 through 14, below.

Figure 12:
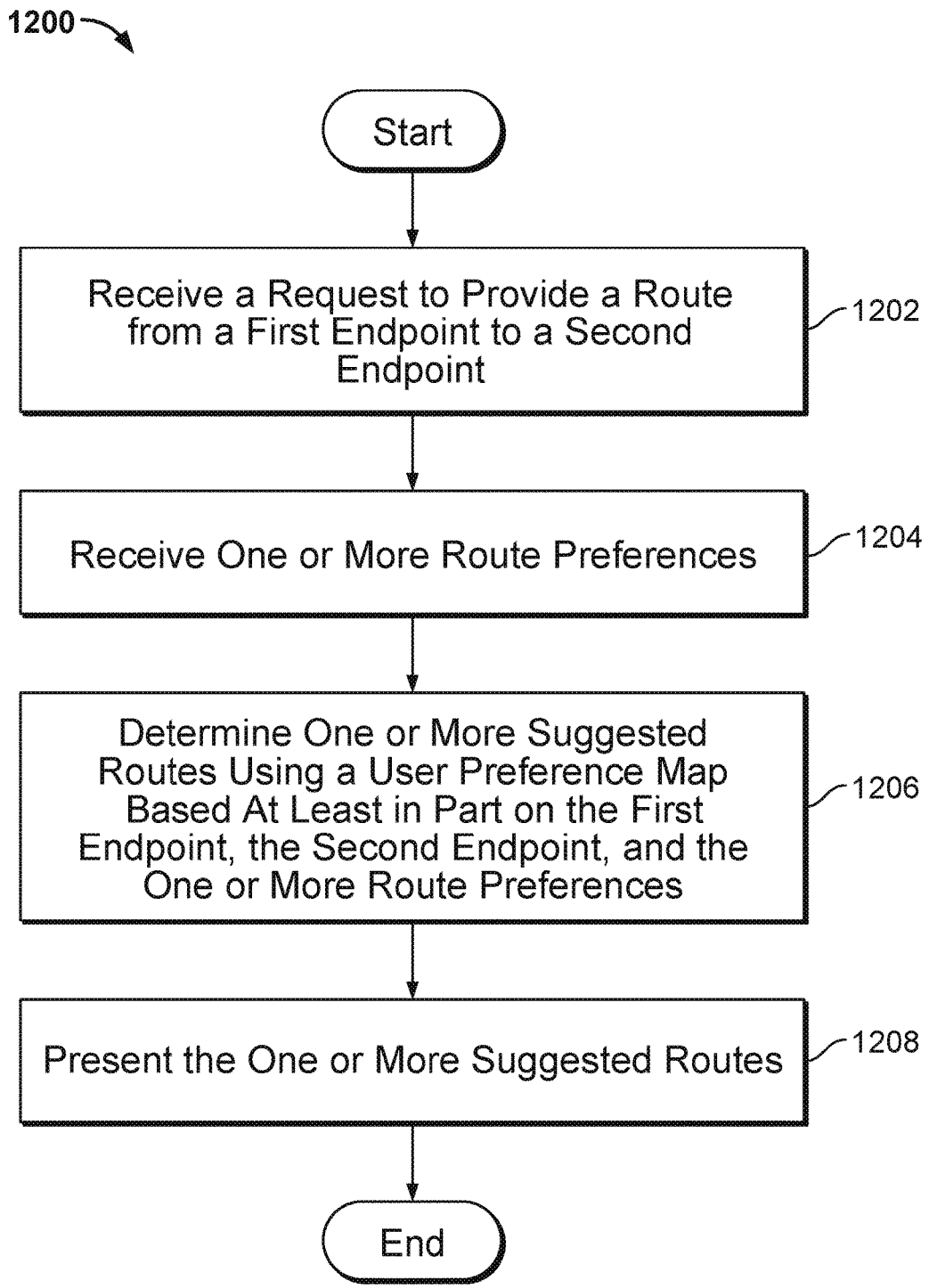
FIG. 12 is a flow diagram showing a process for determining one or more suggested routes using a user preference map in accordance with some embodiments.

FIG. 12 is a flow diagram showing a process for determining one or more suggested routes using a user preference map in accordance with some embodiments. In some embodiments, process 1200 is implemented at system 100 of FIG. 1. In some embodiments, process 1200 is used to implement step 306, at least in part, of process 300 of FIG. 3.

Process 1200 describes an example process for enabling a user to plan routes based on desired route preferences using a user preference map. Process 1200 allows the user to customize the presentation of the data stored in the user preference map to suit his or her route preferences. In some embodiments, process 1200 can be performed prior to or after a user activity. In some embodiments, process 1200 can be performed during an ongoing user activity.

At 1202, a request to provide a route from a first endpoint to a second endpoint is received. The request may be received via a user interface of a device. Each of the first endpoint and the second endpoint represents geographic information associated with a start and end of a desired route. In a first example, each of the first endpoint and the second endpoint can be input by a user as markers dropped on a map application. In a second example, each of the first endpoint and the second endpoint can be input by a user as GPS coordinates. In a third example, each of the first endpoint and the second endpoint can be input by a user as addresses. In various embodiments, the request to provide the route may also include an activity type.

At 1204, one or more route preferences are received. Additional user inputs including route preferences are also received. For example, the route preferences may also be received via a user interface of a device and/or from stored profile data associated with the user. For example, the route preferences can be input by a user making various selections at the user interface. In various embodiments, route preferences describe desired characteristics of a route. Example route preferences may include one or more of the following: a desired distance of the route, a desired surface type associated with the route, a desired (e.g., average or highest) elevation associated with a route, a desired degree of popularity associated with the route, a desired power usage associated with the route, and a preference for whether the route should be the more scenic or the shortest distance route between the first endpoint to the second endpoint.

Another route preference may include a time frame associated with when the route is desired to be traversed.

At 1206, one or more suggested routes are determined using a user preference map based at least in part on the first endpoint, the second endpoint, and the one or more route preferences. A stored user preference map associated with the activity type specified in the request is retrieved. The user inputs of the first endpoint, the second endpoint, and the one or more route preferences are compared to the metadata associated with each edge of the user preference map to find the one or more suggested routes between the first endpoint and the second endpoint that best matches the route preferences. In some embodiments, a route comprises one or more edges. For example, a set of edges that can be traversed from the first endpoint and the second endpoint is first determined and then the metadata stored with each edge is compared to the user preferences to determine one or more routes, each including one or more edges, that best match the user preferences. In the event that a time frame was received as a user route preference, then, for example, only the metadata stored for edges within the specified time frame is used to determine one or more routes, each including one or more edges, that best match the user input route preferences.

The determined one or more routes are presented as suggested routes.

At 1208, the one or more suggested routes are presented. The suggested routes are presented at a map application displayed at a user interface. In some embodiments, additional information associated with each suggested route is also presented with each suggested route at the user interface. For example, additional information associated with each suggested route may include the total route distance, the elevation associated with various locations along the route, the predicted traversal time, the surface type(s) associated with the route, an associated popularity of the route, a predicted power usage associated with the route, and whether the route is expected to be scenic or not.

Figure 13:
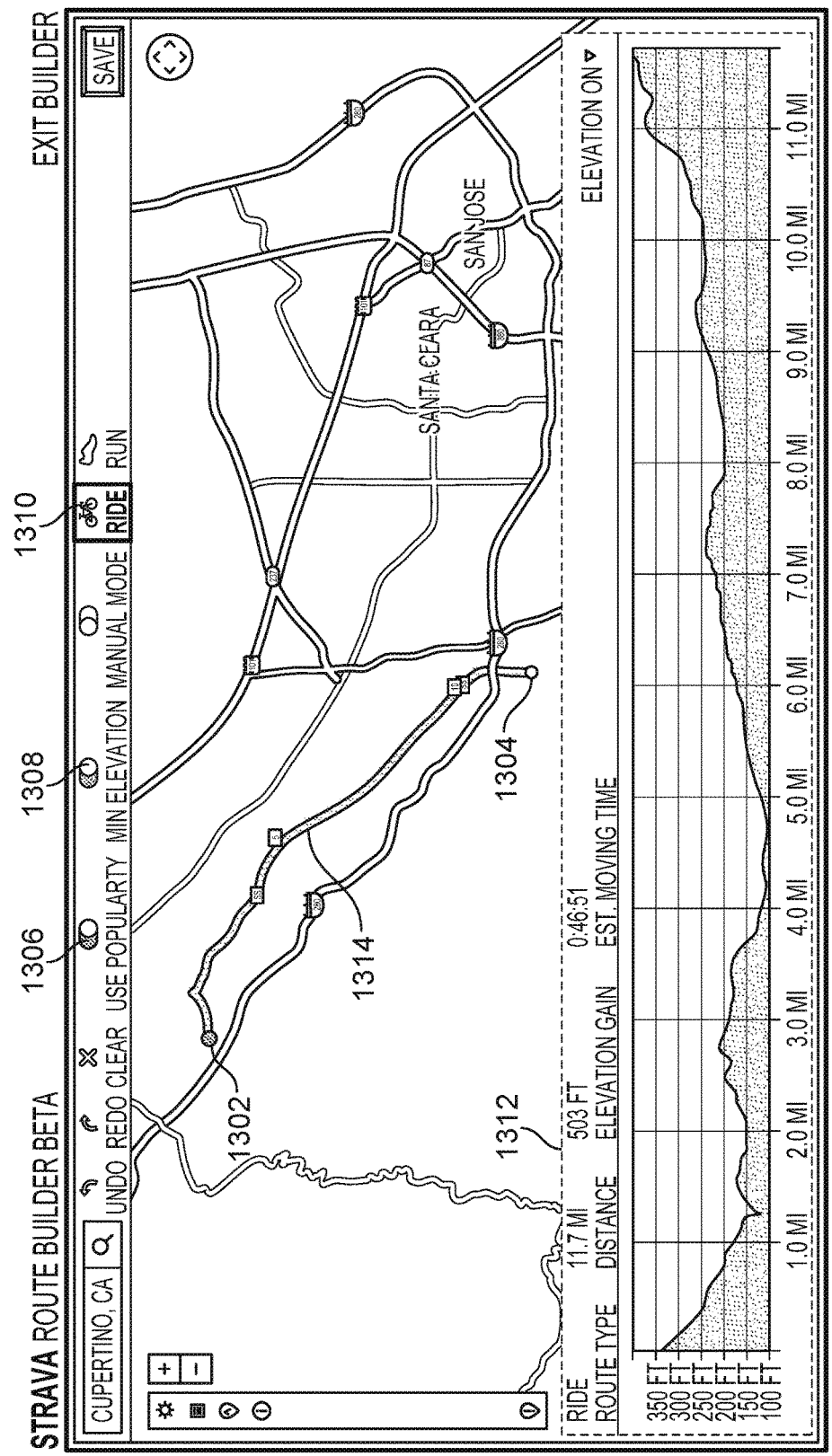
FIG. 13 is a diagram showing an example of presenting a suggested route in accordance with some embodiments.

FIG. 13 is a diagram showing an example of presenting a suggested route in accordance with some embodiments. In some embodiments, suggested route 1314 was determined using a user preference map and a process such as process 1200 of FIG. 12. In some embodiments, suggested route 1314 between first endpoint 1302 and second endpoint 1304 that is presented on a map at a user interface in the example of FIG. 13 is presented in response to receipt of several user inputs at the user interface. First endpoint 1302 and second endpoint 1304 were dropped as markers on the map by a user. Other user inputs associated with route preferences were received through selections at the user interface. "Ride" activity type selection 1310 was selected by a user to indicate that he or she desired to receive a suggested route that is determined based on cycling user activities. "Use popularity" toggle 1306 was selected by a user to indicate that he or she desired to receive a suggested route between first endpoint 1302 and second endpoint 1304 that is popular among users. "Min. Elevation" toggle 1308 was selected by a user to indicate that he or she desired to receive a suggested route between first endpoint 1302 and second endpoint 1304 that minimizes the elevation. Suggested route 1314 was a route that was determined using the user preference map to best match the received user inputs. Additional information regarding suggested route 1314 is displayed in area 1312. The additional information includes the indication that the route type is for a cycling activity, the distance of the route (11.7 miles), the elevation gain (503 feet), the estimated moving time (46:51 minutes), and the elevation profile along various points of the route.

Figure 14:
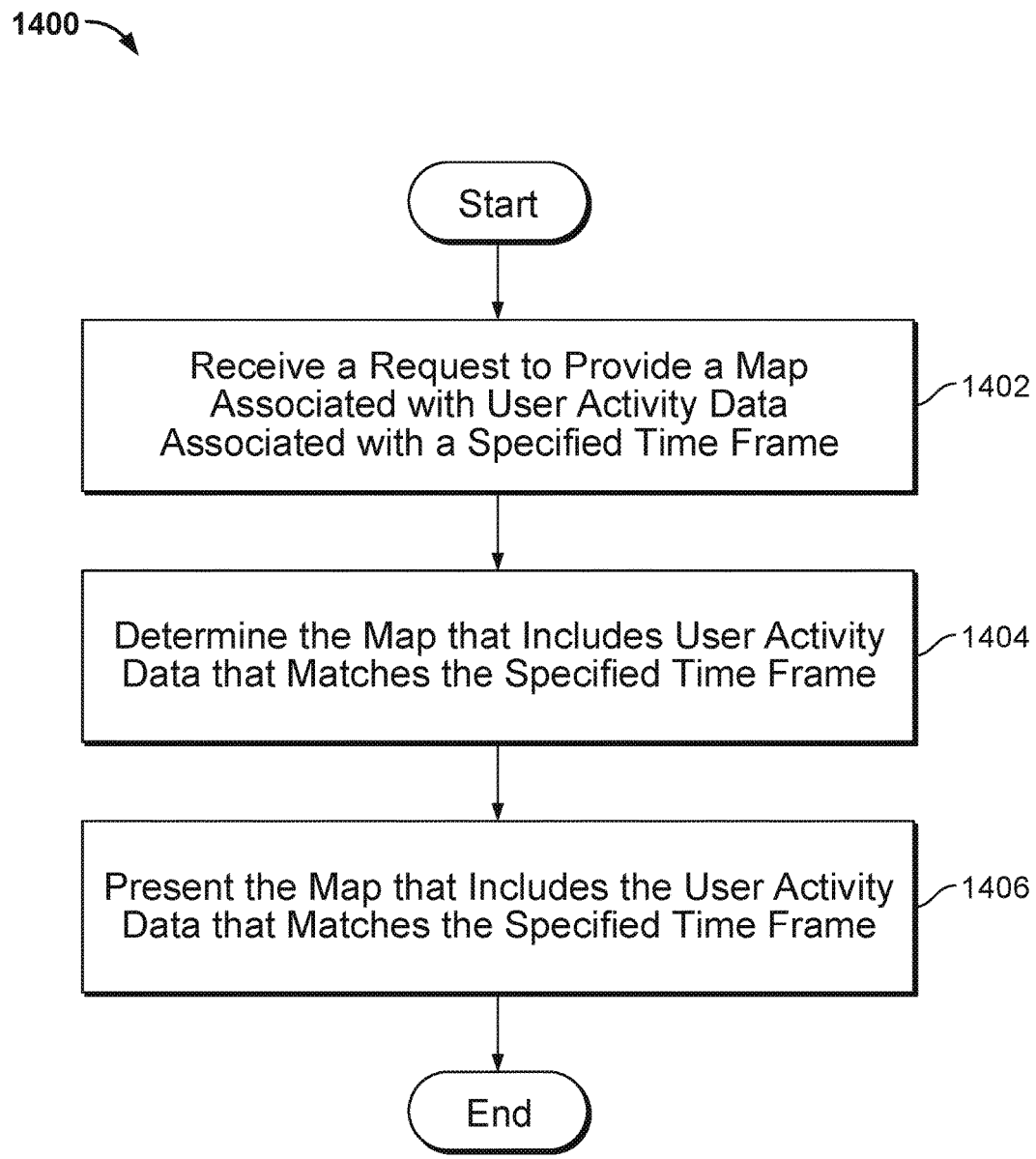
FIG. 14 is a flow diagram showing a process for determining a presentation of a user preference map in accordance with some embodiments.

FIG. 14 is a flow diagram showing a process for determining a presentation of a user preference map in accordance with some embodiments. In some embodiments, process 1400 is implemented at system 100 of FIG. 1.

Process 1400 describes an example process for enabling a user to customize the presentation of a user preference map associated with a specified time frame. As described above, in some embodiments, the metadata stored with edges in the user preference map are associated with time intervals. Process 1400 allows the user to filter out metadata stored with edges in the user preference map that are not associated with the specified time frame, which may include one or more time intervals. Visualizing the user activity data of the user preference map that matches the specified time frame can help a user, such as a city planner, understand traffic patterns during different times of the day, seasons of a year, where there is road construction, before and/or after the installation of a new piece of infrastructure, etc., for example.

At 1402, a request to provide a map associated with user activity data associated with a specified time frame is received. The request may be received via a user interface of a device. The specified time frame describes the times/durations at which user activity data is of interest to a user. In a first example, the specified time frame may comprise a time period across multiple days (e.g., morning and evening commute times across the last year). In a second example, the specified time frame may comprise a time period during a single day (e.g., 5:00 am to 10:00 am on Jun. 13, 2014). In various embodiments, the request to provide the route may also include an activity type.

At 1404, the map that includes user activity data that matches the specified time frame is determined. A stored user preference map associated with the activity type specified in the request is retrieved. The metadata stored with edges in the user preference map that matches the specified time frame is queried and obtained. For example, at least one attribute from the obtained metadata stored with each edge in the user preference map can be visualized and displayed on the map. For example, the number of user activities that was determined to match each edge may be considered as a degree of popularity associated with that edge. The popularities of different edges may be visualized and displayed at the map in a manner such that the relative popularities of the edges can be presented.

At 1406, the map that includes the user activity data that matches the specified time frame is presented. For example, the more popular edges may be displayed in a different opacity or a different color than less popular edges.

In some embodiments, process 1400 may be performed two or more times to determine maps associated with different time frames so that the user can observe a comparison between the characteristics of user activities at each of those different time frames. In some embodiments, a delta map can be created between two maps generated at different time frames to more clearly show the difference in user activity data during those two different times. This delta map can be presented at a user interface.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system, comprising:
 a processor configured to:
  collect a plurality of user activities recorded by a plurality of GPS recording devices, wherein to collect the plurality of user activities comprises to mine user activity data based at least in part on an order associated with a plurality of GPS recording device types; and
  aggregate the plurality of user activities to a base map to generate a user preference map; and
 a memory coupled to the processor and configured to provide the processor with instructions.

2. The system of claim 1, wherein the base map comprises a set of geographical information system (GIS) data.

3. The system of claim 1, wherein to aggregate the plurality of user activities to the base map to generate the user preference map comprises to:
 determine a subset of the plurality of user activities that matches an edge of the base map; and
 store metadata associated with the subset of the plurality of user activities that matches the edge of the base map in the user preference map.

4. The system of claim 3, wherein to determine the subset of the plurality of user activities that matches the edge of the base map comprises to:
 generate a respective buffer at each of one or more locations along the edge;
 include a first user activity included in the plurality of user activities that matches the respective buffer at each of the one or more locations along the edge in the subset of the plurality of user activities that matches the edge; and
 filter out a second user activity included in the subset of the plurality of user activities that matches the edge that comprises non-contiguous points across the respective buffer at each of the one or more locations along the edge.

5. The system of claim 3, wherein to store the metadata associated with the subset of the plurality of user activities that matches the edge of the base map in the user preference map comprises to:
- determine a number of user activities associated with the subset of the plurality of user activities that matches the edge;
- determine a first portion of the number of user activities associated with traversal of the edge in a first direction;
- determine a first traversal time associated with the first portion of the number of user activities associated with traversal of the edge in the first direction;
- determine a second portion of the number of user activities associated with traversal of the edge in a second direction; and
- determine a second traversal time associated with the second portion of the number of user activities associated with traversal of the edge in the second direction.

6. The system of claim 3, wherein to store the metadata associated with the subset of the plurality of user activities that matches the edge of the base map in the user preference map comprises to:
- for a user activity included in the subset of the plurality of user activities that matches the edge, determine a start time associated with the user activity and an amount of time elapsed after the start time that the user activity had matched the edge;
- for a preset time interval in a preset period, determine one or more user activities of the subset of the plurality of user activities that matches the edge in the preset time interval; and
- store metadata associated with the one or more user activities with the preset time interval with respect to the edge in the user preference map.

7. The system of claim 3, wherein to store the metadata associated with the subset of the plurality of user activities that matches the edge of the base map in the user preference map comprises to:
- select a barometric data candidate user activity included in the subset of the plurality of user activities that matches the edge; and
- normalize a recorded elevation corresponding to each of at least a subset of a plurality of data points associated with the selected barometric data candidate user activity based at least in part on obtained elevation data associated with the edge.

8. The system of claim 1, wherein the processor is further configured to present the user preference map.

9. The system of claim 1, wherein the processor is further configured to:
- receive one or more user input route preferences, a user input first endpoint, and a user input second endpoint; and
- determine one or more suggested routes between the user input first endpoint and the user input second endpoint based at least in part on the user preference map based at least in part on the one or more user input route preferences.

10. The system of claim 9, wherein the one or more suggested routes between the user input first endpoint and the user input second endpoint are determined by comparing stored metadata corresponding to one or more edges of the user preference map to the one or more user input route preferences to determine matching edges between the user input first endpoint and the user input second endpoint.

11. A method, comprising:
- collecting a plurality of user activities recorded by a plurality of GPS recording devices wherein collecting the plurality of user activities comprises collecting the plurality of user activities recorded by the plurality of GPS recording devices comprises mining user activity data based at least in part on an order associated with a plurality of GPS recording device types; and
- aggregating the plurality of user activities to a base map to generate a user preference map.

12. The method of claim 11, wherein the base map comprises a set of geographical information system (GIS) data.

13. The method of claim 11, wherein aggregating the plurality of user activities to the base map to generate the user preference map comprises:
- determining a subset of the plurality of user activities that matches an edge of the base map; and
- storing metadata associated with the subset of the plurality of user activities that matches the edge of the base map in the user preference map.

14. The method of claim 13, wherein determining the subset of the plurality of user activities that matches the edge of the base map comprises:
- generating a respective buffer at each of one or more locations along the edge;
- including a first user activity included in the plurality of user activities that matches the respective buffer at each of the one or more locations along the edge in the subset of the plurality of user activities that matches the edge; and
- filtering out a second user activity included in the subset of the plurality of user activities that matches the edge that comprises non-contiguous points across the respective buffer at each of the one or more locations along the edge.

15. The method of claim 13, wherein storing the metadata associated with the subset of the plurality of user activities that matches the edge of the base map in the user preference map comprises:
- determining a number of user activities associated with the subset of the plurality of user activities that matches the edge;
- determining a first portion of the number of user activities associated with traversal of the edge in a first direction;
- determining a first traversal time associated with the first portion of the number of user activities associated with traversal of the edge in the first direction;
- determining a second portion of the number of user activities associated with traversal of the edge in a second direction; and
- determining a second traversal time associated with the second portion of the number of user activities associated with traversal of the edge in the second direction.

16. The method of claim 13, wherein storing the metadata associated with the subset of the plurality of user activities that matches the edge of the base map in the user preference map comprises:
- for a user activity included in the subset of the plurality of user activities that matches the edge, determining a start time associated with the user activity and an amount of time elapsed after the start time that the user activity had matched the edge;
- for a preset time interval in a preset period, determining one or more user activities of the subset of the plurality of user activities that matches the edge in the preset time interval; and storing metadata associated with the one or more user activities with the preset time interval with respect to the edge in the user preference map.

17. The method of claim 13, wherein storing the metadata associated with the subset of the plurality of user activities that matches the edge of the base map in the user preference map comprises:
selecting a barometric data candidate user activity included in the subset of the plurality of user activities that matches the edge; and
normalizing a recorded elevation corresponding to each of at least a subset of a plurality of data points associated with the selected barometric data candidate user activity based at least in part on obtained elevation data associated with the edge.

18. The method of claim 11, further comprising presenting the user preference map.

19. The method of claim 11, further comprising:
receiving one or more user input route preferences, a user input first endpoint, and a user input second endpoint; and
determining one or more suggested routes between the user input first endpoint and the user input second endpoint based at least in part on the user preference map based at least in part on the one or more user input route preferences.

20. The method of claim 19, wherein the one or more suggested routes between the user input first endpoint and the user input second endpoint are determined by comparing stored metadata corresponding to one or more edges of the user preference map to the one or more user input route preferences to determine matching edges between the user input first endpoint and the user input second endpoint.

21. A computer program product, the computer program product being embodied in a non-transitory computer readable storage medium and comprising computer instructions for:
collecting a plurality of user activities recorded by a plurality of GPS recording devices wherein collecting the plurality of user activities comprises collecting the plurality of user activities recorded by the plurality of GPS recording devices comprises mining user activity data based at least in part on an order associated with a plurality of GPS recording device types; and
aggregating the plurality of user activities to a base map to generate a user preference map.

22. The computer program product of claim 21, wherein the base map comprises a set of geographical information system (GIS) data.

23. The computer program product of claim 21, wherein aggregating the plurality of user activities to the base map to generate the user preference map comprises:
determining a subset of the plurality of user activities that matches an edge of the base map; and
storing metadata associated with the subset of the plurality of user activities that matches the edge of the base map in the user preference map.

24. The computer program product of claim 23, wherein determining the subset of the plurality of user activities that matches the edge of the base map comprises:
generating a respective buffer at each of one or more locations along the edge;
including a first user activity included in the plurality of user activities that matches the respective buffer at each of the one or more locations along the edge in the subset of the plurality of user activities that matches the edge; and
filtering out a second user activity included in the subset of the plurality of user activities that matches the edge that comprises non-contiguous points across the respective buffer at each of the one or more locations along the edge.

25. The computer program product of claim 23, wherein storing the metadata associated with the subset of the plurality of user activities that matches the edge of the base map in the user preference map comprises:
determining a number of user activities associated with the subset of the plurality of user activities that matches the edge;
determining a first portion of the number of user activities associated with traversal of the edge in a first direction;
determining a first traversal time associated with the first portion of the number of user activities associated with traversal of the edge in the first direction;
determining a second portion of the number of user activities associated with traversal of the edge in a second direction; and
determining a second traversal time associated with the second portion of the number of user activities associated with traversal of the edge in the second direction.

26. The computer program product of claim 23, wherein storing the metadata associated with the subset of the plurality of user activities that matches the edge of the base map in the user preference map comprises:
for a user activity included in the subset of the plurality of user activities that matches the edge, determining a start time associated with the user activity and an amount of time elapsed after the start time that the user activity had matched the edge;
for a preset time interval in a preset period, determining one or more user activities of the subset of the plurality of user activities that matches the edge in the preset time interval; and
storing metadata associated with the one or more user activities with the preset time interval with respect to the edge in the user preference map.

27. The computer program product of claim 23, wherein storing the metadata associated with the subset of the plurality of user activities that matches the edge of the base map in the user preference map comprises:
selecting a barometric data candidate user activity included in the subset of the plurality of user activities that matches the edge; and
normalizing a recorded elevation corresponding to each of at least a subset of a plurality of data points associated with the selected barometric data candidate user activity based at least in part on obtained elevation data associated with the edge.

28. The computer program product of claim 21, further comprising presenting the user preference map.

29. The computer program product of claim 21, further comprising:
receiving one or more user input route preferences, a user input first endpoint, and a user input second endpoint; and
determining one or more suggested routes between the user input first endpoint and the user input second endpoint based at least in part on the user preference map based at least in part on the one or more user input route preferences.

30. The computer program product of claim 29, wherein the one or more suggested routes between the user input first endpoint and the user input second endpoint are determined by comparing stored metadata corresponding to one or more edges of the user preference map to the one or more user input route preferences to determine matching edges between the user input first endpoint and the user input second endpoint.

* * * * *